United States Patent [19]

Kurane et al.

[11] Patent Number: 5,378,832
[45] Date of Patent: Jan. 3, 1995

[54] POLYSACCHARIDE AND A METHOD OF PRODUCING IT

[75] Inventors: Ryuichiro Kurane, Ibaraki; Yasuhiro Nohata, Mie; Michio Shiomi; Shuichi Ishino, both of Yamaguchi; Akira Yotsuji, Tokyo; Hideki Murata, Yamaguchi, all of Japan; Seiji Sugimoto, Brookline, Mass.

[73] Assignees: Agency of Industrial Science and Technology; Kyowa Hokkoh Kogyo Co., Ltd., both of Tokyo, Japan

[21] Appl. No.: 94,091

[22] PCT Filed: Jul. 20, 1993

[86] PCT No.: PCT/JP92/00695
§ 371 Date: Jul. 20, 1993
§ 102(e) Date: Jul. 20, 1993

[87] PCT Pub. No.: WO93/11163
PCT Pub. Date: Jun. 10, 1993

[30] Foreign Application Priority Data
Nov. 29, 1991 [JP] Japan .................................. 3-316391

[51] Int. Cl.$^6$ .......................... C12N 1/20; C12P 19/04; B01F 17/56; C08B 37/00
[52] U.S. Cl. .................................. 536/123.1; 435/101; 435/829; 536/123; 604/367
[58] Field of Search ................ 435/829, 101; 536/123, 536/123.1

[56] References Cited

U.S. PATENT DOCUMENTS 5,175,279 12/1992 Kurane et al. .

FOREIGN PATENT DOCUMENTS 0023397 4/1981 European Pat. Off. .
0064354 4/1984 European Pat. Off. .
2058107 4/1981 United Kingdom .

*Primary Examiner*—Herbert J. Lilling
*Attorney, Agent, or Firm*—Sughrue, Mion, Zinn, Macpeak & Seas

[57] ABSTRACT

The present invention provides a polymer comprising a polysaccharide having excellent water absorption properties, moisture absorption properties, moisture retention properties and thickening properties. Said polysaccharide has the following properties: (A) the principal constituents of the sugar composition are rhamnose, fucose, glucose and glucuronic acid which are present in a molar ratio of (1-4):2:(1-8):(1-4); (B) elemental analysis (wt %):
C: 36 ±3
H: 7 ±1
O: 56 ±4,
containing 9–13% of crystalline water
(C) solubility:
slightly soluble in water; soluble in alkalies; insoluble in methanol, ethanol and acetone;
(D) UV absorption spectrum:
no absorption detected at 280 nm characteristic of proteins (peptides) or at 260 nm characteristic of nucleic acids; and
(E) IR absorption spectrum:
an absorption pattern characteristic of polysaccharides is observed near 800–1200$^{-i}$ Said polysaccharide is produced by a fermentation method using a natural medium or a synthetic medium of Alcaligenes microorganism.

4 Claims, 24 Drawing Sheets

① RHAMNOSE
② FUCOSE
③ GLUCOSE
④ MANNOSE

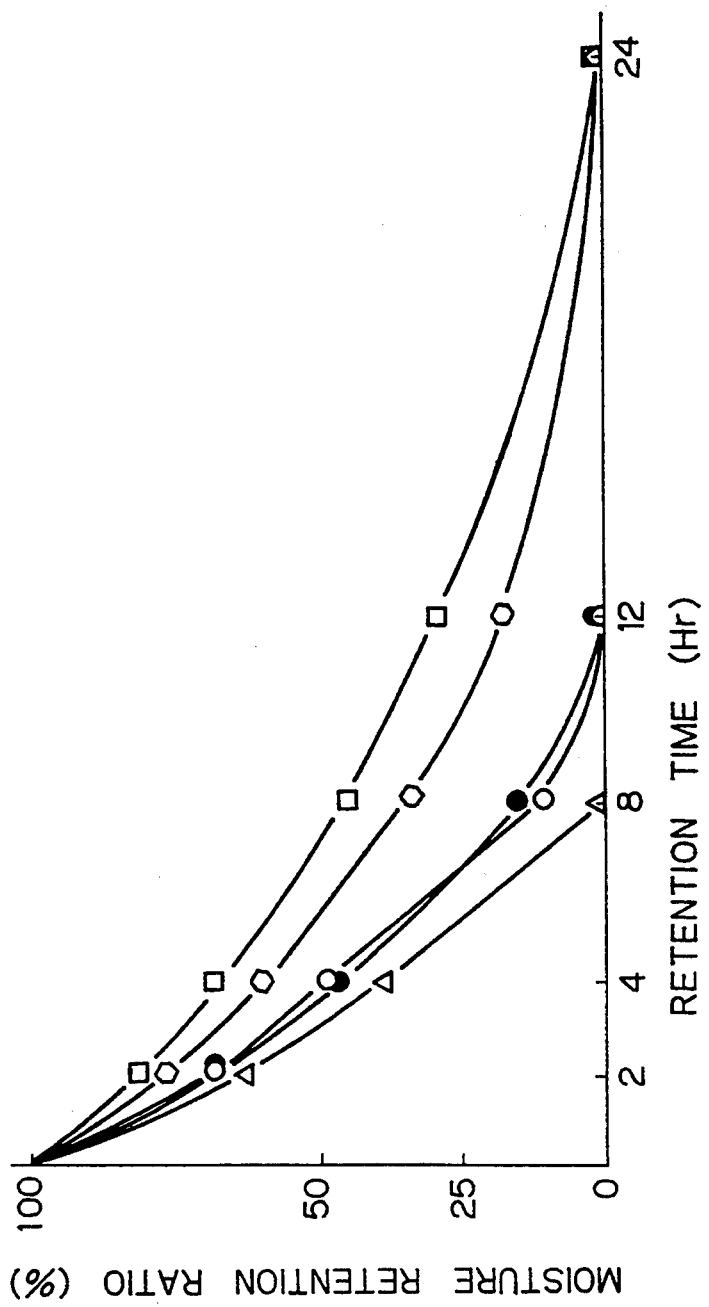

POLYSACCHARIDE AND A METHOD OF PRODUCING IT

The present invention relates to a microorganism-derived polysaccharide and a method of producing it, further to water absorbents, moisture absorbents or humectants and thickening agents comprising mainly polysaccharide. The present invention is expected to find use in a broad range of applications including water absorbents, moisture absorbents, humectants and thickening agents such as sanitary articles and paper diapers, cosmetics and even covering humectants for the irrigation of seedlings to be used in the greening of deserts.

BACKGROUND ART

With recent changes in life styles, the consumption of sanitary articles and paper diapers is steadily increasing. Most water absorbents, moisture absorbents or humectants and thickening agents used in sanitary articles and paper diapers are based on synthetic high polymer materials. Since currently available sanitary articles and paper diapers are of a disposable type, they are disposed of in flush toilets and discharged into the environment. However, they are essentially not biodegradable and therefore remain in the environment for a prolonged period of time. This is not only unseemly but also deleterious to the environment. Thus, the development of alternatives that are biodegradable and which are hence compatible with the maintenance of a healthy environment is strongly desired.

Similarly, with recent advances in biotechnology, attempts have been made to incorporate biomaterials in cosmetics. However, the use of such "biocosmetics" is very limited and there has been a growing need for the development of new organism-derived moisture absorbents or humectants that can be used as a base for cosmetics.

Desertification is an environmental problem affecting the ecology of the entire earth. Japan is making a contribution to the greening of deserts by supplying Egypt and other such countries with synthetic high polymer water absorbents, moisture absorbents and humectants for use to retain water for irrigating seedlings. If such water absorbents, moisture absorbents or humectants are organism-derived and are biodegradable and compatible with the environment, no harm results from their use in the growing of seedlings.

However, microorganism-derived biopolymers are usually expensive, in comparison with synthetic high polymers, thereby limiting the range of their utilization. In addition, there are many cases wherein synthetic high polymers are formed into various shapes after they have been dissolved or dispersed in organic solvents in commercial production. Accordingly, it is a general consideration that if microorganism-derived biopolymers are treated with an organic solvent, such functions will be impaired. Hence, the range of their application has been generally limited. If such biodegradable biopolymers which are compatible with the environment are treated with an organic solvent without any deterioration in their functions resulting therefrom, application could be envisaged in various fields, including the field of chemical industries and their use will be remarkably advantageous.

Accordingly, in order for biopolymers to be formed in various shapes and to have a wide range of applications, it is essential that their properties should not be caused to deteriorate after they are dissolved or dispersed in organic solvents broadly used in the field of chemical industries. Thus, the biopolymers have come to be used as starting materials for products in various chemical industries.

The object of the present invention therefore is to provide a polymer containing a polysaccharide that overcomes and eliminates the problems associated with synthetic high polymer water absorbents, moisture absorbents or humectants and which, hence, is highly biodegradable and can be used without adversely affecting the environment giving problems such as secondary pollution and which, in addition, has a high water absorption capability, moisture absorption capability, moisture retention capability and thickening capability, having resistance to organic solvents.

With respect to the fermentation and production of polysaccharides, methods using saccharides (fructose and sucrose), inorganic materials and natural medium components (concretely, yeast extracts) have been reported (Japanese Patent Public Disclosure No. 291292/1990).

It has also been found that said polysaccharides can be fermented and produced by adding fructose, sucrose and glucose as saccharides to natural medium components such as yeast extracts, polypeptone and CSL. It is anticipated that when natural medium components are used, components may become unhomogeneous and hence the fermentation and production of said polysaccharides may become unstable. The present inventors have conducted studies and aimed at establishing synthetic mediums which contain no natural component, are cheap to produce and have good workability. As a result, they have found that said polysaccharides can be fermented and produced by synthetic mediums comprising a saccharide, an inorganic salt, an amino acid mixed solution and a trace metal salt mixed solution. It is another object of the present invention to determine their conditions.

DISCLOSURE OF THE INVENTION

The present inventors have studied in detail biopolymers having high water absorption properties, moisture retention properties, water retention properties and thickening properties relating to, for example, polysaccharides described in Japanese Patent Public Disclosure No. 291292/1990 which are dissolved or dispersed in organic solvents; namely, active components of polysaccharides described in the above patent application. Consequently, they have invented a method of producing polymers containing polysaccharides having a high moisture absorption capability, moisture retention capability, water absorption capability and thickening capability even after they are dissolved or dispersed in organic solvents and heated, and subsequently solvents are evaporated, by separating components having a molecular weight of $1 \times 10^6$ or more.

The present invention relates to a polymer containing a polysaccharide, namely, a novel material separated from the polysaccharide described in the above patent application. More specifically, the present invention relates to a polymer containing a polysaccharide having water absorption properties, moisture retention properties, moisture absorption properties and thickening properties, which is novelly obtained by separating high molecular components alone from a polysaccharide produced by an Alcaligenes microorganism, typically *Alcaligenes latus* strain B-16 (FERM BP-2015).

In the present invention, investigation of medium components has been carried out in the fermentation and production of said polysaccharide. As a result, it has been found that said polysaccharide can be fermented and produced according to both a natural medium using natural medium components and a synthetic medium comprising a saccharide, an inorganic salt, an amino acid mixed solution and a trace metal salt mixed solution.

BRIEF DESCRIPTION OF DRAWINGS

FIG. 9 (B) shows a mass spectrum for rhamnose of trimethylsilylated derivatives of the hydrolyzate of the material obtained in accordance with the present invention. In FIG. 9 the vertical axis plots the intensity and the horizontal axis plots m/e.

FIG. 10 (B) shows a mass spectrum for fucose of trimethylsilylated derivatives of the hydrolyzate of the material obtained in accordance with the present invention. In FIG. 10, the vertical axis plots the intensity and the horizontal axis plots m/e.

In FIG. 11 the vertical axis plots the intensity and the horizontal axis plots m/e.

In FIG. 13, (A) shows the viscosity of Kelzan and a non-treated polymer of high molecular components, (B) that of a kerosene-treated polymer, (C) that of a xylene-treated polymer, (D) that of a trichloroethane-treated polymer, (E) that of a formamide-treated polymer and (F) that of a DMSO-treated polymer respectively.

In FIG. 14, (A) shows the viscosity of Kelzan and a non-treated polymer of high molecular components, (B) that of a kerosene-treated polymer, (C) that of a xylene-treated polymer, (D) that of a trichloroethane-treated polymer, (E) that of a formamide-treated polymer and (F) that of a DMSO-treated polymer, respectively.

BEST MODE FOR CARRYING OUT THE INVENTION

The present inventors searched for a novel material having resistance to organic solvents and having water absorption properties, moisture retention properties, moisture absorption properties and thickening properties, by using the polysaccharide described in the above Japanese Patent Public Disclosure No. 1291292/1990. As a result, they have obtained a high molecular component with a molecular weight of $1 \times 10^6$ or more.

Figure 1:
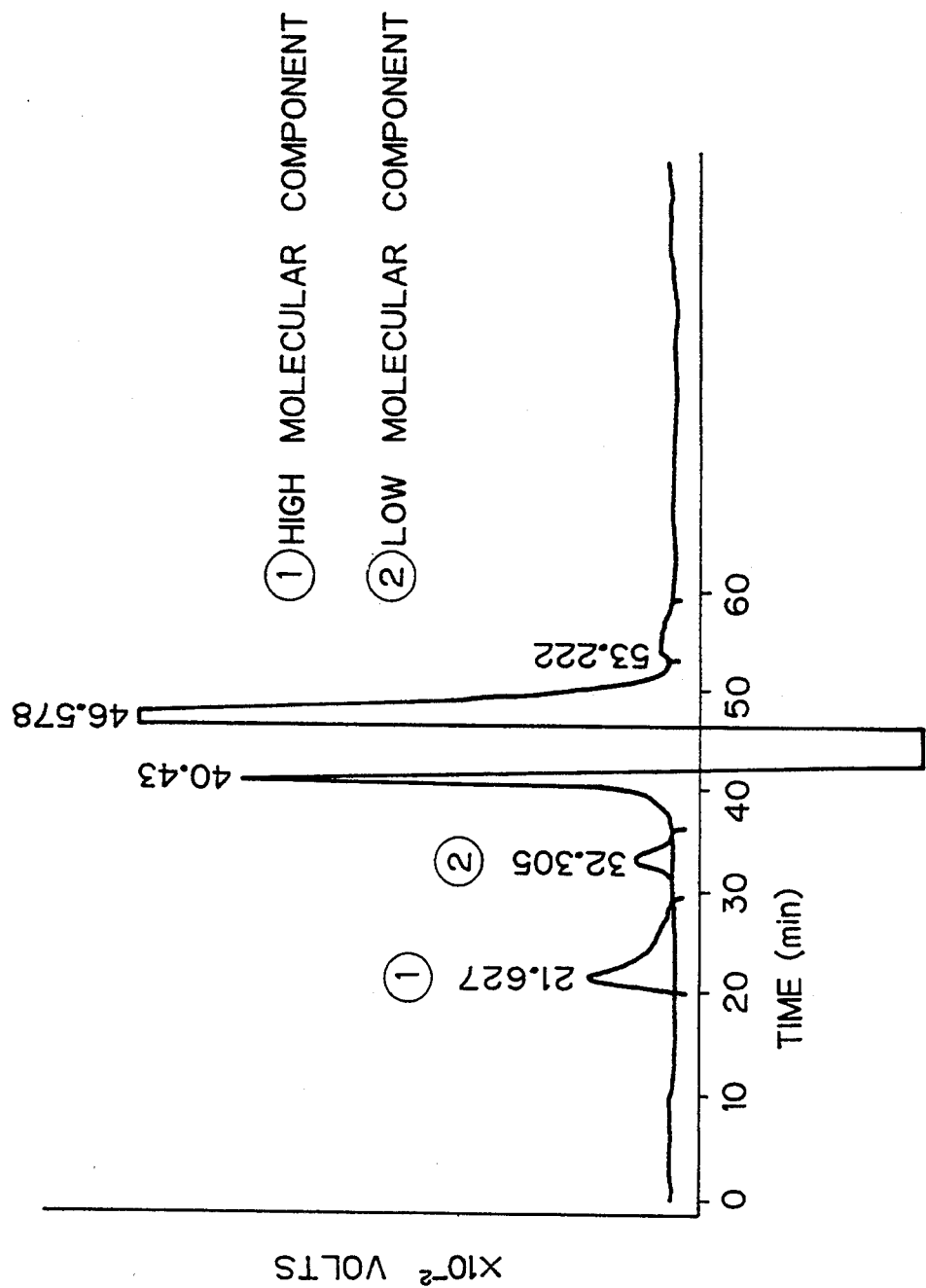
FIG. 1 is a high-performance liquid chromatography chart for the polysaccharide described in Japanese Patent Public Disclosure No. 291292/1990. The vertical axis plots the dielectric constant ($\times 10^{-1}$ volt) and the horizontal axis plots the retention time.
Figure 2A:
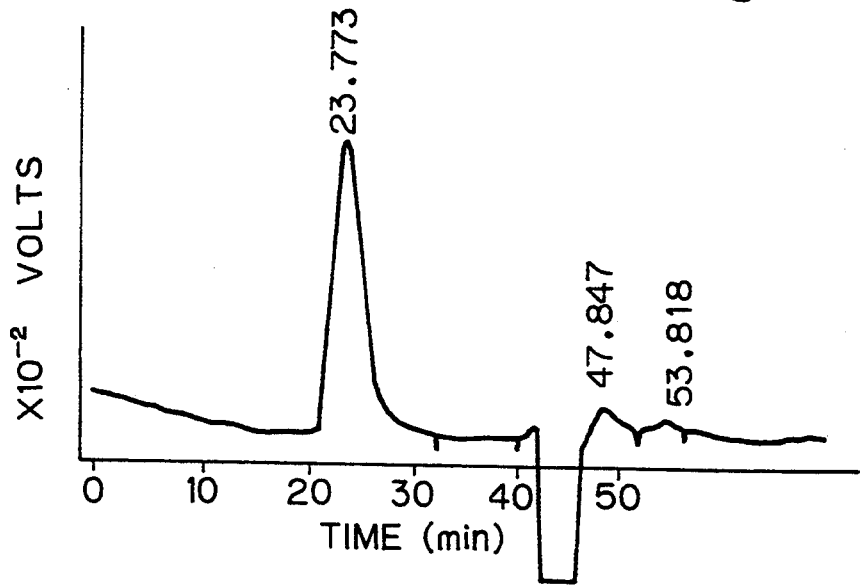
FIG. 2(A), (B), (C) are high-performance liquid chromatography charts for hyaluronic acid with molecular weights of $2.3 \times 10^6$, $3.0 \times 10^5$ and $8.4 \times 10^4$ respectively. The vertical axis plots the dielectric constant ($\times 10^{-2}$ volt) and the horizontal axis plots the retention time.
Figure 2B:
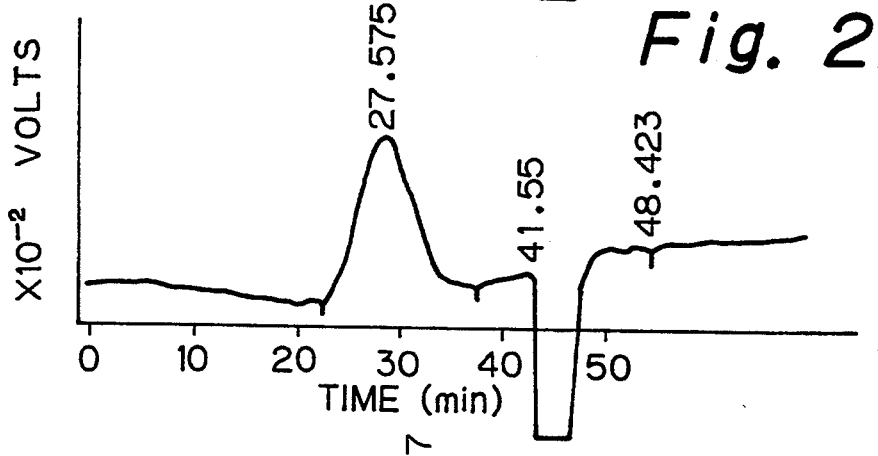
Figure 2C:
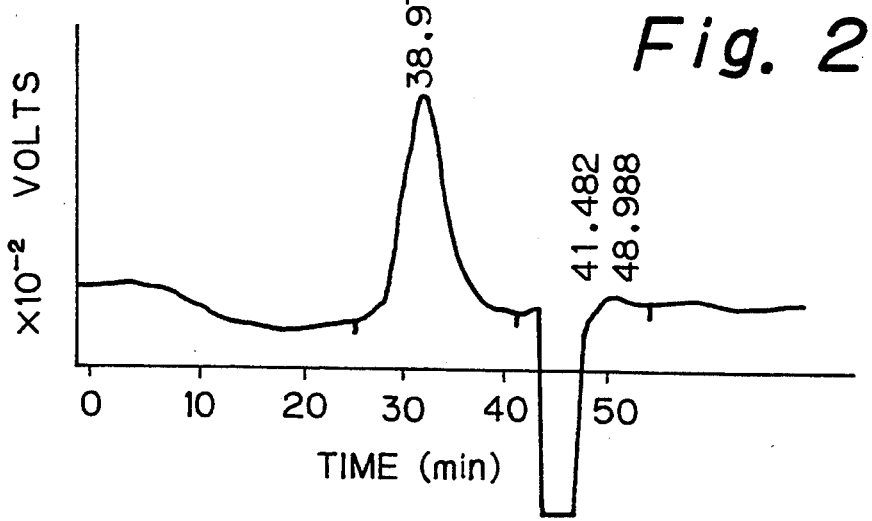

The separation of high molecular components was carried out according to high-performance liquid chromatography (LC-6A, manufactured by Shimazu Seisakusho). As a column, a gel-filtration type, TSKG600pw×L+TSKG3000pw×L (manufactured by Toso) was used. It was carried out under the conditions of a column temperature of 40° C., a mobile phase of 0.2M, an aqueous NaCl solution and 0.5 mL/min RI. The polysaccharide of the above patent application diluted to 1000 ppm and then measured is shown in FIG. 1 and the hyaluronic acid whose molecular weight is known and which is diluted to 1000 ppm and measured is shown in FIG. 2. As shown in FIG. 1, the polysaccharide described in the above Japanese Patent Public Disclosure is composed of two polymers, each of which shows a peak at the efflux time of 21.627 minutes and at that of 32.305 minutes. The efflux time of the hyaluronic acid having a molecular weight of $2.3 \times 10^6$ shown in FIG. 2(A) was 23.773 minutes. Compared with the hyaluronic acid with a molecular weight of $3.0 \times 10^5$ shown in FIG. 2(B) and that with a molecular weight of $8.6 \times 10^4$ shown in FIG. 2(C), it has been revealed that the polysaccharide of the above patent application is a polymer having a molecular weight of $1 \times 10^6$ or more.

A polymer having a molecular weight of $1 \times 10^6$ or more was isolated and its physical properties were examined. Consequently, it was revealed that it has remarkably high water absorption properties, moisture absorption properties, moisture retention properties and thickening properties, compared with the polysaccharide described in the above patent application, which has led to the completion of the present invention.

The polysaccharide of the present invention has the Following properties:

(1) sugar composition as determined by thin-layer chromatography, liquid chromatography and gas chromatography:
  the principal constituents are rhamnose, fucose, glucose and glucuronic acid which are present in a molar ratio of (1-4):2:(1-8):(1-4);

(2) elemental analysis (wt%):
  (said polysaccharide containing 9-13% of crystalline water)
  C: 36±3
  H: 7±1
  O:56±4;

(3) solubility:
  slightly soluble in water (neutral); soluble in alkalies; insoluble in methanol, ethanol and acetone;

(4) UV absorption spectrum
  no absorption detected at 280 nm characteristic of proteins (peptides) or at 260 nm characteristic of nucleic acids; and (5) IR absorption spectrum:
  an absorption pattern characteristic of polysaccharides is observed near 800-1200 $cm^{-1}$; CH and $CH_2$ absorption patterns due to carbohydrates are observed near 2950 $cm^{-1}$; and an OH absorption pattern due to carbohydrates is observed near 3400±20 $cm^{-1}$.

Any microorganism can be used in the present invention so far as it belongs to the genus Alcaligenes and has the ability to produce the polysaccharide of the present invention. For example, microorganisms belonging to *Alcaligenes latus* can be used. A concrete, preferable example is *Alcaligenes latus* strain B-16, which has been deposited with the Fermentation Research Institute, the Agency of Industrial Science and Technology, under accession number FERM BP-2015.

The mediums found in accordance with the present invention are a natural medium employing a saccharide such as glucose, fructose, sucrose or maltose, an inorganic salt such as potassium phosphate, sodium phosphate, magnesium sulfate, magnesium chloride, sodium chloride, urea, ammonium chloride or ammonium sulfate, and a natural medium constituent such as yeast extract, peptone, polypeptone, casamino acid or CSL; and a synthetic medium using as basical medium constituents a saccharide such as glucose, fucose, lactose, sucrose or maltose, an inorganic salt such as potassium phosphate, sodium phosphate, magnesium sulfate, magnesium chloride, sodium chloride, urea, ammonium chloride or ammonium sulfate, and an amino acid mixed solution as a natural organic component, and adding a trace metal salt mixed solution and a vitamin mixed solution as a factor for the growth stabilization or the producibility stabilization. As the concentration of each medium constituent, a natural medium constituent can be used in the range of 0.1-1%, a saccharide in the range of 1-4%, an inorganic salt in the range of 0.01-0.1%, an amino acid mixed solution in the range of 10-1000 mg/L and each constituent of a trace metal salt mixed solution in the range of 0.03-10 mg/L. As amino acids, any amino acid can be used so far as it exists naturally. More specifically, an amino acid which is composed of at least 2 selected from Arg, Cit, Orn, Val, Ile, Met, Gly, Glu, Leu, Pro, His and Tyr can be used. They can be used singly, too. As a trace metal salt, a mixed solution composed of at least one selected from sulfate, hydrochloride and nitrate of Fe, Ca, Mn, Zn and Cu, sodium molybdate, sodium tungsten acid and sodium borate can be mentioned. More specifically, a mixture of ferrous sulfate and calcium chloride can be used. They can be used singly, too. As a vitamin mixed solution, a mixture of vitamin B, nicotinic acid, pantothenic acid, paramino benzoate, ribonic acid and biotin can be used. They can be used singly, too.

The cultivation is carried out according to shake incubation or agitation incubation under aerobic conditions usually for 1-10 days. The cultivation temperature is preferably in the range of 15°-40° C. pH is adjusted to 4-10, preferably near neutral. After the completion of the cultivation, the recovery of said polysaccharide is performed according to the ethanol precipitation described in Japanese Patent Public Disclosure No. 291292/1990.

EXAMPLES

Hereunder, the present invention will be explained in more detail according to Examples.

Example 1

A. Recovery of polysaccharide components with a molecular weight of about $1 \times 10^6$ or more Sucrose (15 g), $KH_2PO_4$ (6.8 g), $K_2HPO_4$ (8.8 g), $MgSO_4 \cdot 7H_2O$ (0.2 g), NaCl (0.1 g), urea (0.5 g) and meat extract (0.5 g) were dissolved in 1,000 mL of distilled water and the medium was adjusted to a pH of 7.4. A portion (150 mL) of the medium was transferred into a 500-mL conical flask and sterilized by autoclaving at 102° C. for 15 minutes. Thereafter, a loopful of *Alcaligenes latus* strain B-16 (FERM BP-2015) was inoculated into the medium in the flask and subjected to rotary shaking culture at 30° C. (180 rpm).

Figure 3:
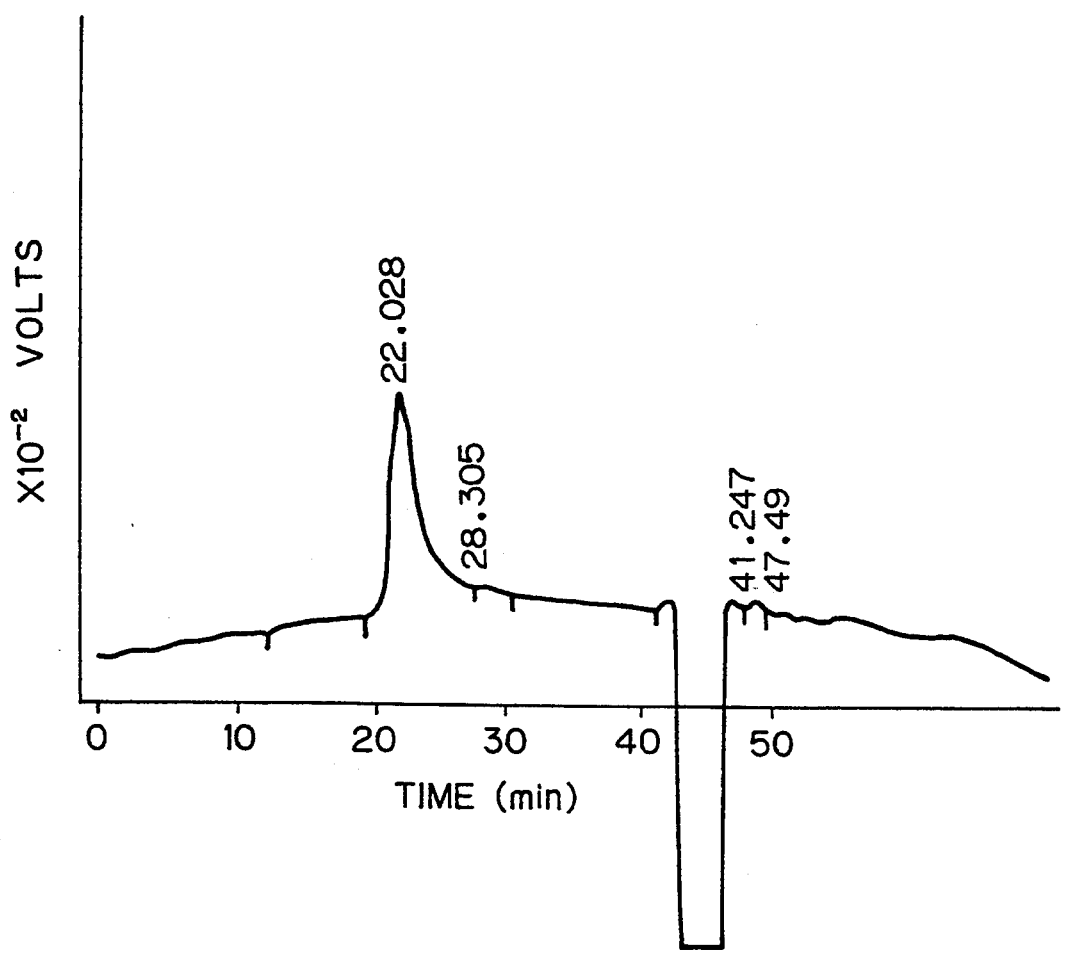
FIG. 3 is a high-performance liquid chromatography chart for a polymer containing the polysaccharide of high molecular components of the present invention. The vertical axis plots the dielectric constant ($\times 10^{-2}$ volt) and the horizontal axis plots the retention time.

After 6 days of cultivation, polysaccharide components with a molecular weight of $1 \times 10^6$ or more were recovered from the culture broth by the following procedure. Namely, 4,000 mL of water was added to 1,000 mL of the culture broth and the medium was adjusted to a pH of 12 with NaOH. Subsequently, the resultant medium was treated in a 1,000-mL column, Diaion HPA-75 (OH−) (manufactured by Mitsubishi Kasel) at 8 Rv or less. Here, the removal of proteins, nucleic acids and low-molecular components was carried out. Then, the removal of cells was carried out by means of a membrane filter of a filtration auxiliary RL700 (Radiolight)+5 μm. The cell-free liquid was neutralized to a pH of 7 with HCl and concentrated. The precipitate was recovered with two volumes of acetone. It was washed with ten volumes of acetone five times. Then, the precipitate was vacuum-dried at room temperatures to obtain a white purified high-molecular polymer. In order to determine that high-molecular components alone are separated, an HPLC chart shown in FIG. 3 was prepared.

Figure 4:
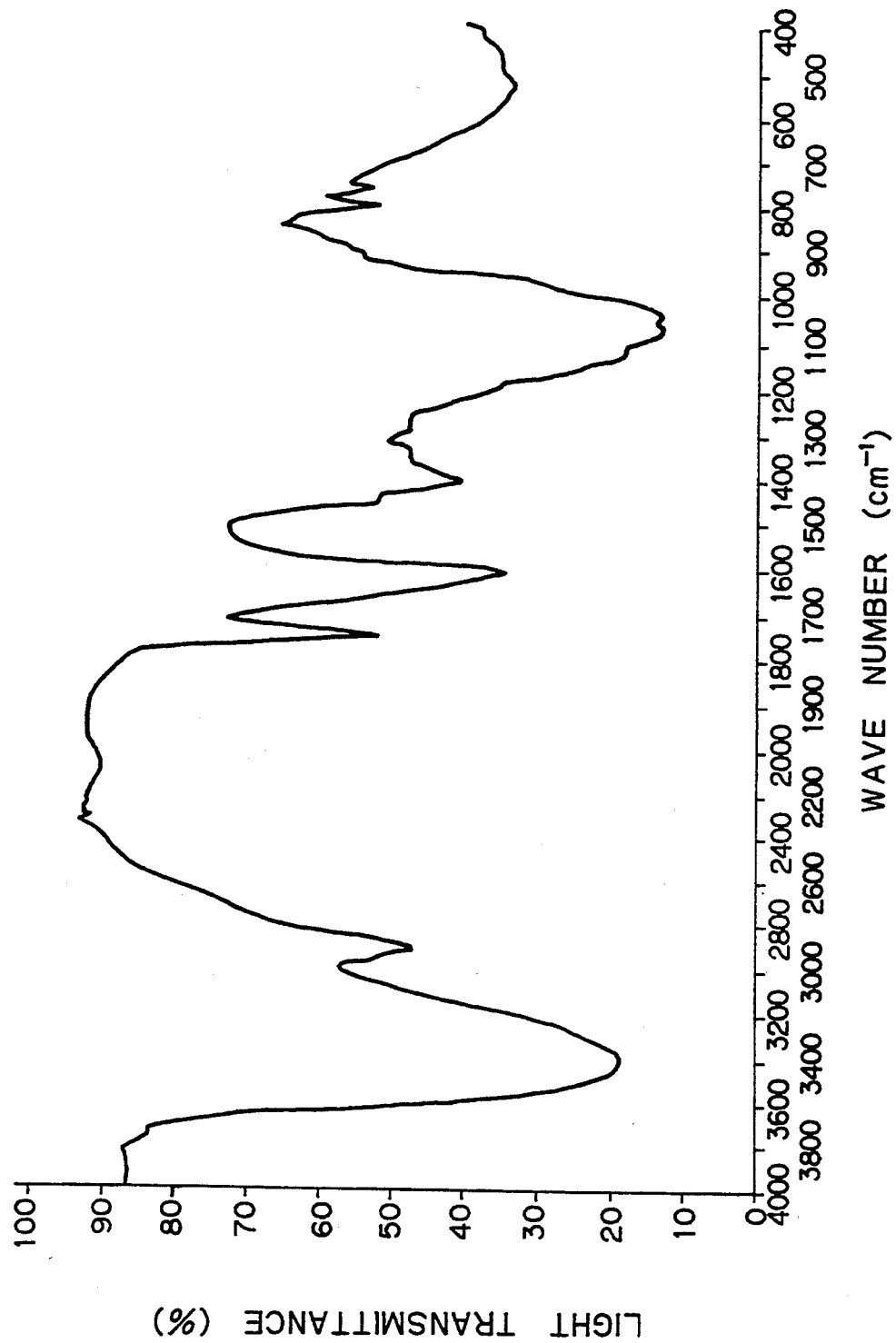
FIG. 4 is an IR absorption spectrum of the material obtained in accordance with the present invention. The vertical axis plots the light transmittance (%) and the horizontal axis plots the wave number ($cm^-$).

The high-molecular polymer obtained in Example 1 had the following physicochemical properties:
(1) Color: white
(2) Carbonization temperature: 225°–280° C.
(3) Elemental analysis:
   Carbon and hydrogen contents were determined with a Carlo Erba C & H Analyzer. The oxygen content was calculated by subtracting the sum of C and H contents from 100 (wt%):
   C: 36±3
   H: 7±1
   O: 56±4
(4) Solubility:
   Slightly soluble in water (neutral); soluble in alkalies; insoluble in methanol, ethanol and acetone
(5) IR absorption spectrum:
   As shown in FIG. 4, an absorption pattern characteristic of polysaccharides was observed near 800–1,200 $cm^{-1}$; an absorption pattern characteristic of uronic acid was observed at 1620±20 $cm^{-1}$; CH and $CH_2$ absorption patterns due to carbohydrates were observed near 2950 $cm^{-1}$; and an OH absorption pattern due to carbohydrates was observed near 3400±20 $cm^{-1}$. These results suggest that the polymer would be an acidic polysaccharide chiefly composed of sugars and other carbohydrates.
(6) Qualitative and quantitative reactions on sugars:
   The high-molecular biopolymer obtained in Example 1 was subjected to qualitative and quantitative reactions on sugars.
   In the anthrone reaction and the phenol sulfate procedure, the results were evaluated in terms of glucose. In the Elson-Morgan method, hexosamines (e.g., glucosamine and galactosamine) were used as indicators; in the periodic acid-resorcinol reaction, sialic acids (e.g., N-acetylneuraminic acid and N-glycolylneuraminic acid) were used as indicators; and in the carbazole sulfate reaction, uronic acids (e.g., glucuronic acid and galacturonic acid) were used as indicators. The biopolymers of interest were hydrolyzed by the following scheme. The results of reactions performed on the respective samples are summarized in Table 1.

| Method of Hydrolyzing Polysaccharides |
| --- |
| heat in 2N $H_2SO_4$ at 100° C. for 2 hours |
| (sealed under vacuum) |
| ↓ |
| neutralize with $Ba(OH)_2$ |
| ↓ |
| centrifuge at 18,000 rpm for 5 minutes to remove the precipitate |
| ↓ |
| stir with activated carbon for 5 minutes |
| ↓ |
| centrifuge at 19,000 rpm for 5 minutes to remove the precipitate |
| ↓ |
| filter through 0.45-μm membrane |
| ↓ |
| concentrate with an evaporator at 50° C. |

TABLE 1

Qualitative and Quantitative Reactions of Constituent Sugars

| Reaction | Sugar content in each sample |
| --- | --- |
| Anthrone reaction | 76% |
| Phenol sulfate procedure | 78% |
| Elson-Morgan | — |
| Periodic acid-resorcinol reaction | — |
| Carbazole sulfate reaction | 19% |

In the anthrone reaction and the phenol sulfate procedure, the results were expressed in percentages in terms of glucose. In the carbazol sulfate reaction, they were expressed in terms of glucuronic acid.

The results of the qualitative and quantitative reactions on sugars suggest the possibility that the biopolymers of interest have hexose and uronic acids as constituents. It is, however, clear that the biopolymers do not contain hexamines such as glucosamine or sialic acids such as N-acetylneuraminic acid.

(7) Constituent sugars:
Once it was established that the biopolymers of interest had sugars such as hexose and uronic acids, they were hydrolyzed with an acid such as hydrochloric acid and subjected to identification of constituent sugars by thin-layer chromatography, liquid chromatography, gas chromatography and mass spectroscopy.

(A) Thin-layer chromatography

A hydrolyzate of the high-molecular biopolymer obtained in Example 1 was subjected to thin-layer chromatography. Rf values of known sugars, the polysaccharide described in Japanese Patent Public Disclosure No. 291292/1990 and the hydrolyzate of the sample as obtained for various developing solvents are summarized in Table 2 (comparison of Rf values between each standard sugar and the hydrolyzate of the sample). The following conditions were used to identify constituent sugars by thin-layer chromatographic analysis. Identification of sugars by TLC Experimental conditions:
1. TLC plate
   α) Kiesel Gel 60 of Merck
   β) Silica gel 60A of Whatman
2. Developing temperature
   50° C.
3. Color producing agent
   diphenylamine-aniline-phosphate reagent 4. Developing solvent
 a) t-butanol/acetone/0.1M lactic acid=4/4/2
 b) isopropanol/acetone/0.1M lactic acid=4/4/2
5. Preconditioner of TLC plate
 0.5M NaH$_2$PO$_4$

TABLE 2

Rf Values in Thin-Layer Chromatography of Standard Sugars and Hydrolyzates of the Sample

| Experimental conditions Name of samples | plate α, solvent a, developed twice | plate β, solvent b, developed once |
|---|---|---|
| Sample | 0.04, 0.036, 0.58, 0.78, 0.87, 0.91, 0.95 | 0.41, 0.79, 0.95 |
| Polysaccharide of Japanese Patent Public Disclosure No. 291292/1990 | 0.05, 0.37, 0.45, 0.57, 0.78, 0.88, 0.92, 0.95 | 0.40, 0.52, 0.79, 0.94 |
| D-glucose | 0.33 | 0.40 |
| D-galactose | 0.21 | 0.22 |
| D-mannose | 0.43 | 0.49 |
| D-xylose | 0.55 | 0.65 |
| L-arabinose | 0.50 | 0.46 |
| D-ribose | 0.66 | |
| L-ribose | 0.42 | |
| L-fucose | 0.78 | 0.77 |
| L-rhamnose | 0.91 | 0.92 |
| 2DOX-D-glucose | 0.84 | 0.88 |
| 2DOX-D-ribose | 0.94 | |
| D-glucuronic acid | 0.76, 0.79, 0.83, 0.85, 0.95 | 0.94 |
| D-galacturonic acid | 0.19 | |
| D-galactosamine | 0.03, 0.55, 0.70, 0.83 | |
| D-trehalose | 0.18 | |
| Maltose | 0.19 | 0.24 |
| D-lactose | 0.13, 0.23 | 0.15 |
| D-celbiose | 0.21, 0.94 | |
| Melibiose monohydrate | 0.07 | |
| Methyl-α-D-glucopyranoside | 0.87 | |
| Salicin | 1.0 | |
| Raffinose | 0.06 | |
| Gulose | | 0.48 |
| Allose | | 0.42 |
| Talose | | 0.51 |

The data in Table 2 shows that the biopolymer of interest contains glucose, rhamnose, fucose and glucuronic acid since it has Rf values in agreement with those of glucose, rhamnose, fucose and glucuronic acid, as standard, and accords with the hydrolyzates of the polysaccharide described in Japanese Patent Public Disclosure No. 291292/1990 except mannose.

(B) High-performance liquid chromatography

Figure 5B:
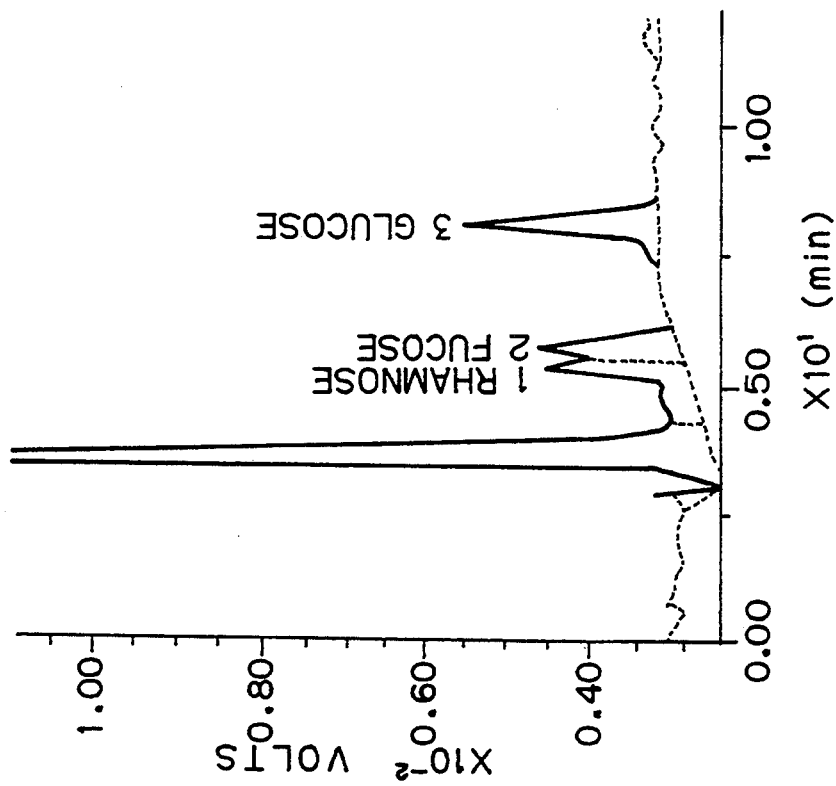
FIG. 5(B) is a high-performance liquid chromatography chart for the hydrolyzate of the material obtained in accordance with the present invention. The vertical and horizontal axes plot the same parameters as in FIG. 5(A).
Figure 5A:
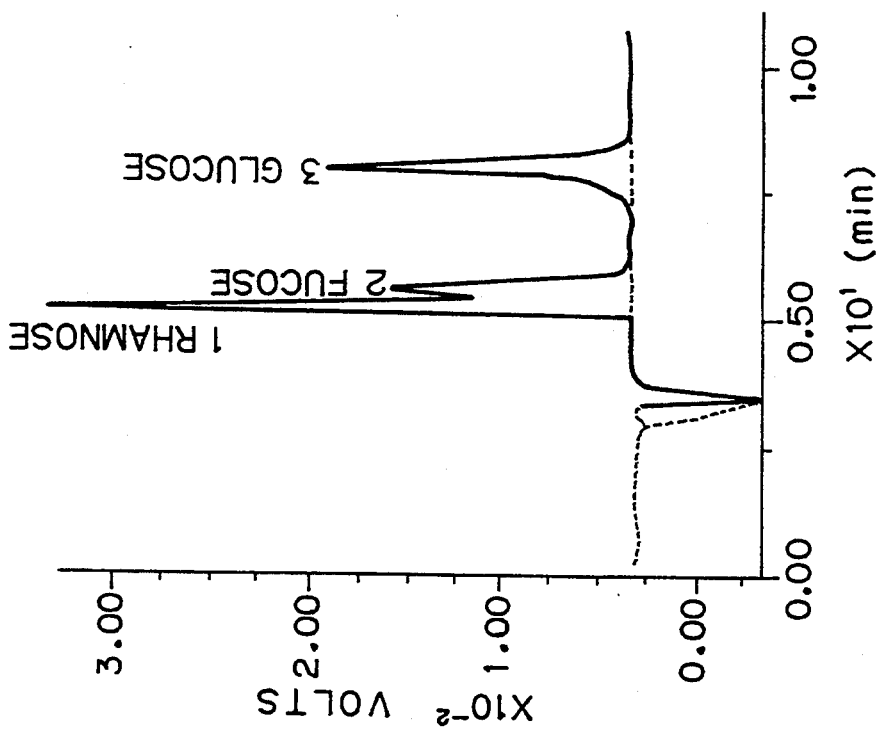
FIG. 5(A) is a high-performance liquid chromatography chart for standard samples (neutral sugars: glucose, rhamnose and fucose). The vertical axis plots the dielectric constant ($\times 10^{-2}$ volt) and the horizontal axis plots the retention time ($\times 10^1$ minutes).
Figure 6:
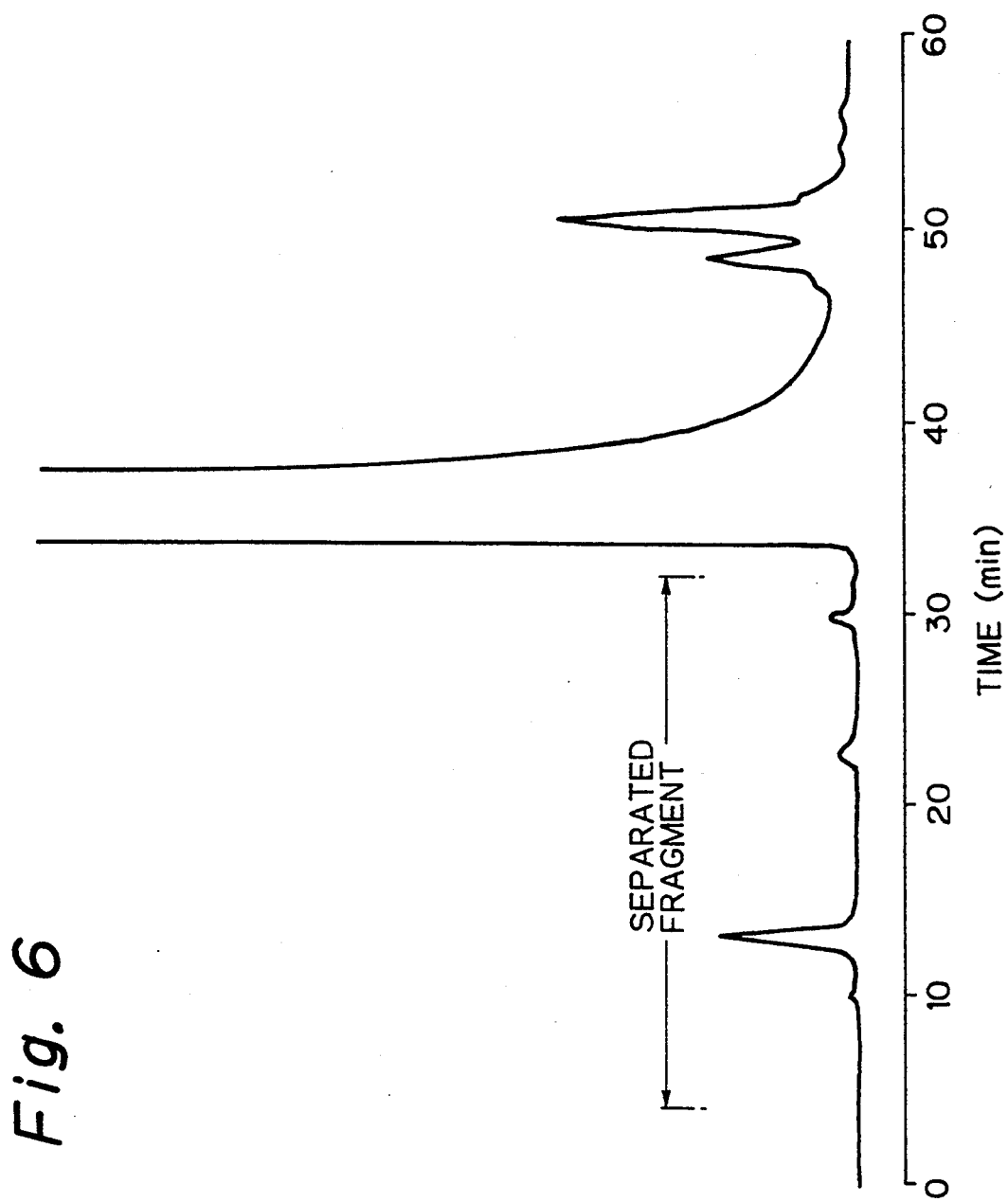
FIG. 6 is an HPLC chart for the hydrolyzate of the polysaccharide of high molecular components, showing that impurities are removed and the necessary part (monosaccharide) is taken out. The horizontal axis plots the retention time (minute) and the vertical axis plots the fluorescent strength.
Figure 7A:
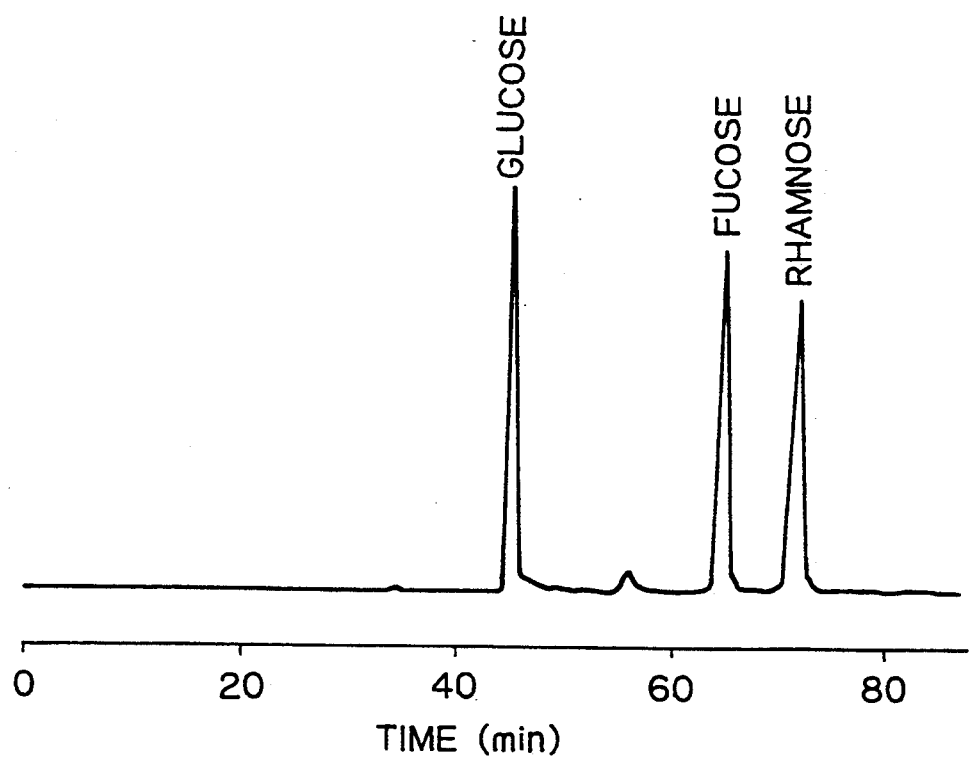
FIG. 7(A) is a graph showing the relationship between the fluorescent strength and the retention time (minute) of the standard samples.

The neutral sugars (rhamnose, fucose, mannose and glucose) identified by thin-layer chromatography were analyzed with high-performance liquid chromatography using Amide-80 (manufactured by Tosoh Corp.) as a column: mobile phase, acetonitrile/water=80/20; flow rate, 1.0 mL/min.; column temperature, 80° C.; detector, RI. Liquid chromatographic charts for the standard samples of the neutral sugars and the hydrolyzate of the biopolymer sample prepared in Example 1 are shown in FIG. 5(A) and FIG. 5(B), respectively. Further, the analysis was conducted by replacing the column with μBondasphere 5 μ, C$_{18}$, 100A (manufactured by Waters, Inc.). The sample was derivated to a 2-aminopyridine using a fluorescent detector (EX 320 nm, Em 400 nm, GainX100, Attn 16). To 20 mL of an aqueous sample solution were added 100 mL of a mixed solution of 4.25 g of 2-AP, 12.5 mL of deionized water, 12.5 mL of methanol and 2 mL of glacial acetic acid and the mixed solution was heated at 100° C. for 20 minutes. To the resultant mixture were added 100 mL of a solution of 1 g of NaBH$_3$CN dissolved in 25 mL of methanol. The obtained solution was heated at 100° C. for 3 hours and cooled spontaneously. Subsequently, analysis was carried out by using Ultrahydrogel 120 (manufactured by Waters, Inc.) (7.8 nm×30 cm, mobile phase: 20 mM, ammonium acetate (pH 7.5), flow rate: 1 mL/min, room temperature). The portion shown in FIG. 6 was fractioned. Then, the hydrolyzate of the biopolymer and standard samples of glucose, rhamnose and fucose were compared by high-performance liquid chromatography using μ Bondasphere 5 μ, C$_{18}$, 100A, 3.9 mm×15 cm three-in-line, mobile phase: 0.1 mol, sodium citrate (pH 4.0)/acetonitrile =99.3/0.7, flow rate: 0.3 mL/min, room temperature). The results are shown in FIG. 7(A) and (B), which reveal that both had the same retention time. The above results show that peak ①of the hydrolyzate of the biopolymer corresponds to rhamnose, peak ②to fucose, and peak ③to glucose, respectively, according to the analysis by high-performance liquid chromatography.

(C) Gas Chromatography and Gas Mass Spectroscopy

In order to perform a triple check on the constituent sugars identified by TLC and HPLC, the biopolymer of interest was subjected to gas chromatography and gas mass spectroscopy (GC-MS). Simultaneous analysis of neutral sugars and uronic acid (glucuronic acid) was performed by the following procedure: the sample obtained in Example 1 was hydrolyzed with HCl, silylated with a silylating agent, loaded into a gas chromatographic column (supported by Silicone OV-101), heated to a temperature in the range of 50°-200° C., and analyzed by FID. Hydrolysis of the sample was conducted in accordance with tile method of hydrolyzing polysaccharides as described above. The hydrolyzate was derivated to a trimethylsilyl form by the following scheme.

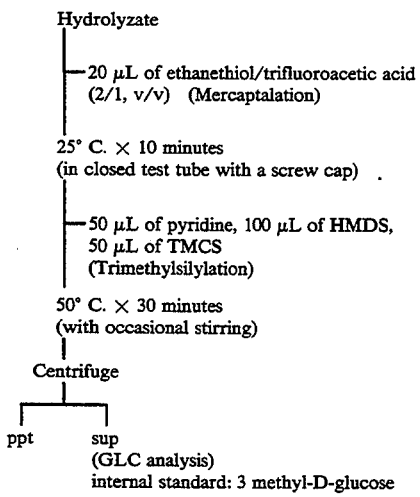

Derivation to Trimethylsilyl

Figure 8A:
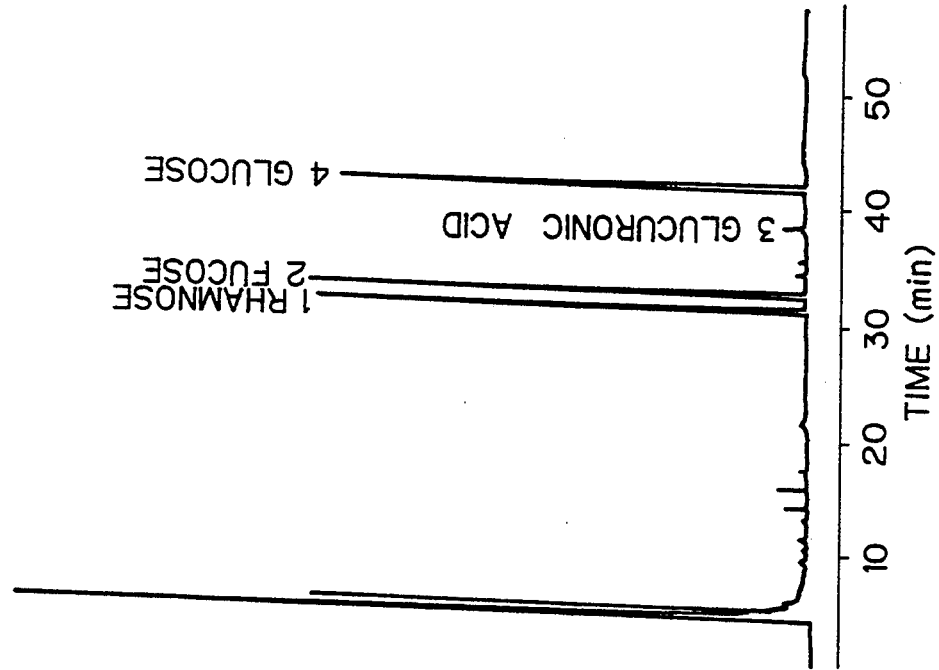
FIG. 8(A) shows a gas chromatography pattern of trimethylsilylated derivatives of standard samples (rhamnose, fucose, glucuronic acid and glucose).
Figure 8B:
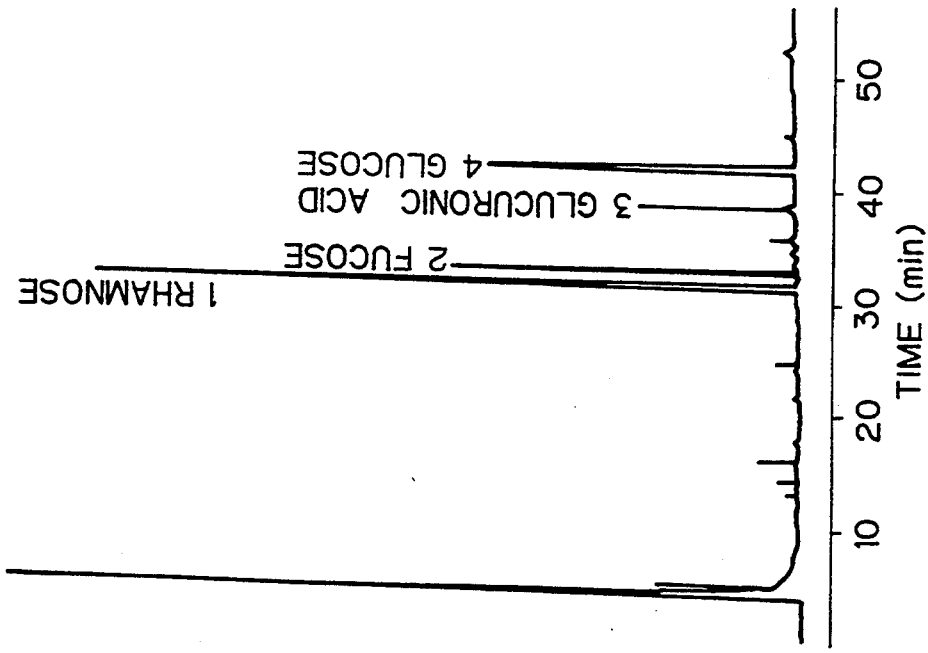
FIG. 8(B) shows a gas chromatography pattern of trimethylsilylated derivatives of the hydrolyzate of the material obtained in accordance with the present invention. In both Fig.(A) and (B), the vertical axis plots the peak height and the horizontal axis plots the retention time (minute).

A gas chromatographic pattern of the authentic samples of trimethylsilylated derivatives of glucose, mannose, rhamnose, fucose and uronic acid (glucuronic acid) is shown in FIG. 8(A). A gas chromatographic pattern of the hydrolyzate of the purified biopolymer obtained in Example 1 is shown in FIG. 8(B). As these figures show, the silylated derivative of the hydrolyzate of the sample of interest was in complete agreement with the silylated derivatives of glucose, rhamnose, fucose and glucuronic acid.

Three peaks that were comparatively large in the gas chromatographic analysis (peak 1, rhamnose; peak 2, fucose; peak 5, glucose) were introduced into a mass spectrograph and subjected to gas mass spectroscopy (GC-MS) analysis.

Figure 9A:
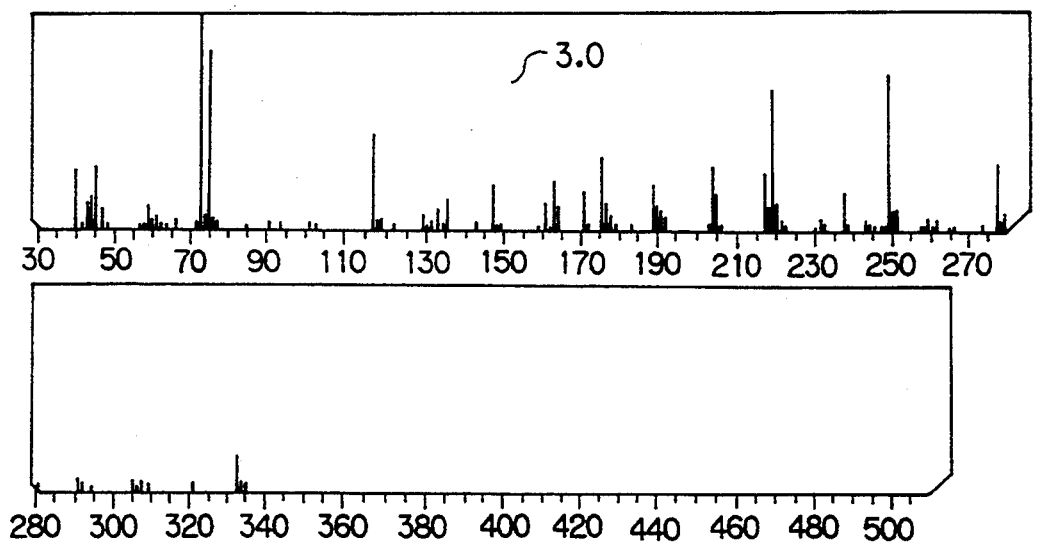
FIG. 9 (A) shows a mass spectrum for rhamnose of trimethylsilylated derivatives of standard samples.
Figure 9B:
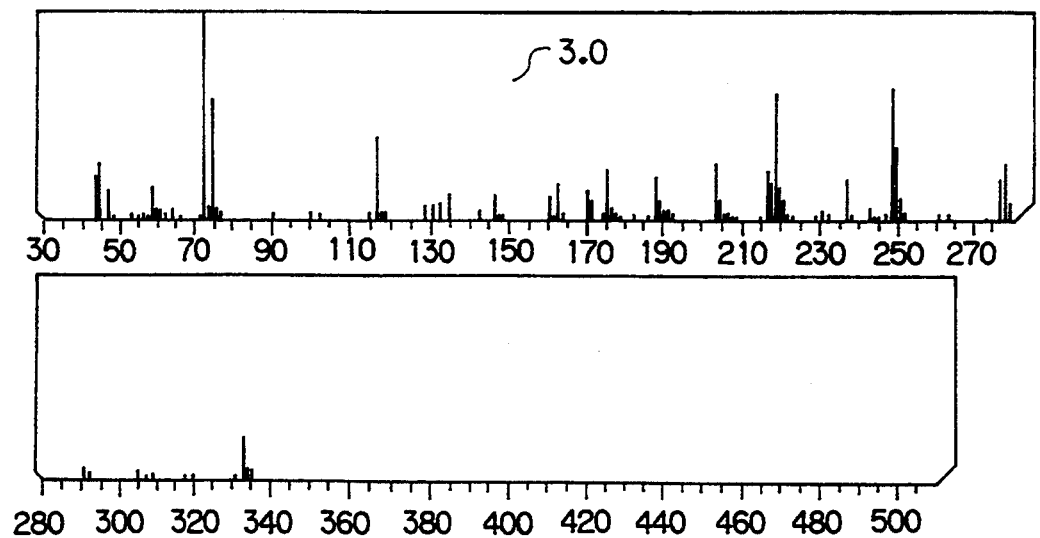
Figure 10A:
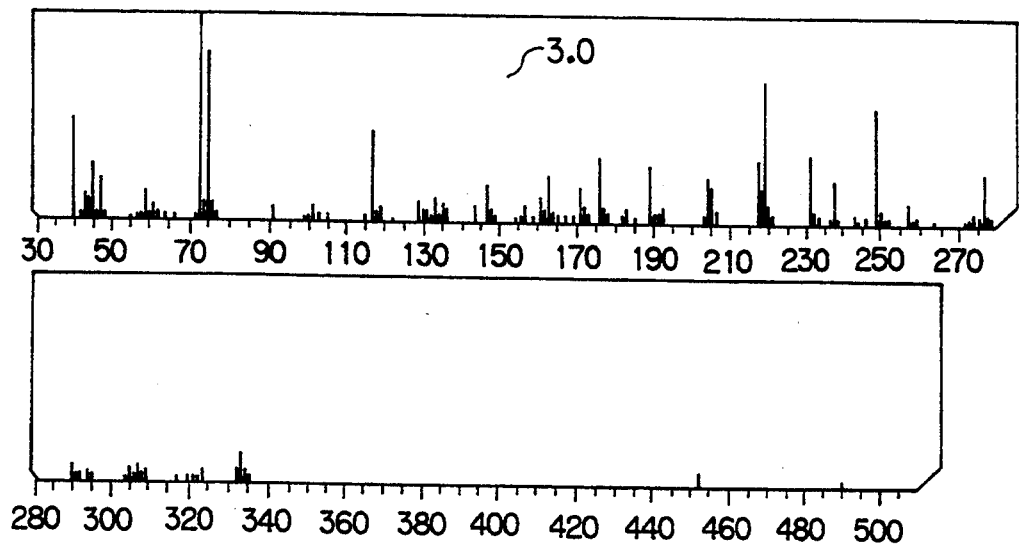
FIG. 10 (A) shows a mass spectrum for fucose of trimethylsilylated derivatives of standard samples.
Figure 10B:
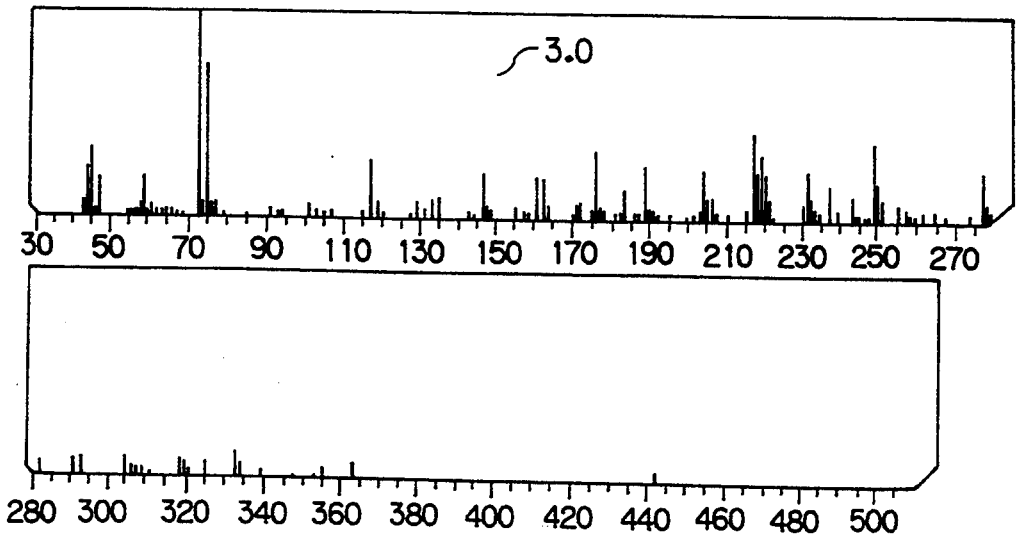
Figure 11A:
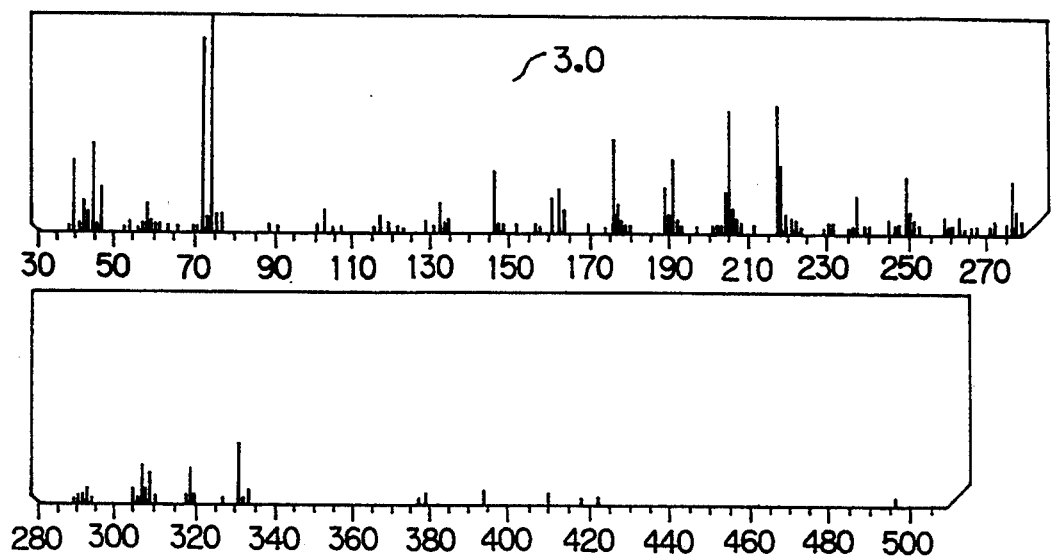
FIG. 11 (A) shows a mass spectrum glucose of trimethylsilylated derivatives of standard samples.
FIG. 11(B) shows a mass spectrum for glucose of dimethylsilylated derivatives of the hydrolyzate of the material obtained in accordance with the present invention.
Figure 11B:
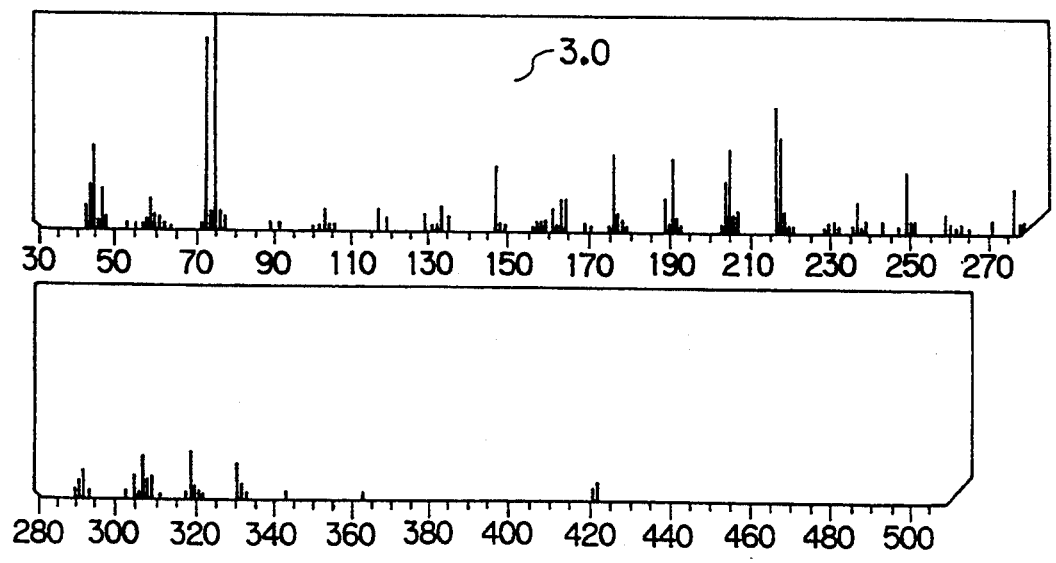

FIG. 9(A) and FIG. 9(B) show the mass spectra of peak 1 and rhamnose for the standard samples and tile hydrolyzate of the biopolymer, respectively; FIG. 10(A) and FIG. 10(B) show the mass spectra of peak 2 and fucose for the standard samples and the hydrolyzate, respectively; and FIG. 11(A) and FIG. 11(B) show the mass spectra of peak 5 and glucose for the standard samples and the hydrolyzate, respectively. As these mass spectra show, the fragments of peaks 1, 2 and 5 are in agreement with those of the standard samples.

Thus, the results of GC-MS analysis also confirm that the hydrolyzate of the biopolymer of interest contained rhamnose, fucose and glucose as constituent sugars.

In summary, the results of gas chromatography (GC) and gas mass spectroscopy (GC-MS) showed that the hydrolyzate of the biopolymer of interest contained glucose, rhamnose, fucose and glucuronic acid as constituent sugars.

(8) Molar ratio of constituent sugars:

The molar ratio of the four constituent sugars, rhamnose, fucose, glucose and glucuronic acid, was determined from the ratio of areas of individual peaks in high-performance liquid chromatography. The conditions of HPLC were the same as those described in (7)-(B). In order to determine the molar ratio of the constituent sugars, the standard samples of specified concentrations were first subjected to HPLC and the areas of peaks obtained were determined. Then, the hydrolyzate of the purified biopolymer obtained in Example 1 (for the conditions of hydrolysis, see (6)) was subjected to HPLC and the areas of peaks obtained were determined. On the basis of the thus determined peak area, the molar ratio of the constituent sugars under consideration was calculated by means of the following equation:

$$\text{Molar ratio of constituent sugar} = \frac{\text{Area of hydrolyzate (constituent sugar)}}{\text{Peak area of standard sample}} \times \text{(Number of moles of standard sample)}$$

Figure 7B:
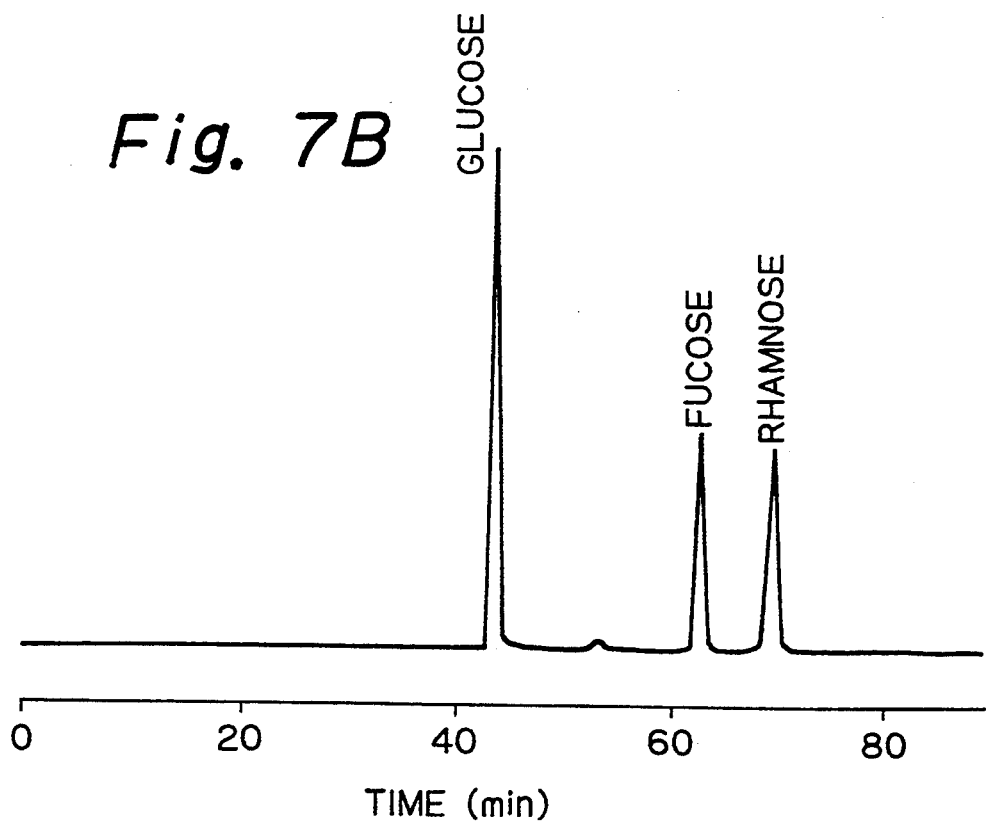
FIG. 7(B) is a graph showing the relationship between the fluorescent strength and the retention time (minute) of the hydrolyzate of the material obtained in accordance with the present invention.

The gas chromatographic pattern of the standard samples used is shown in FIG. 7-(A) and that of the hydrolyzate of the high-molecular biopolymer obtained in Example 1 is shown in FIG. 7-(B). The areas and the number of moles of the standard samples and the hydrolyzate are shown In Table 3.

TABLE 3

Monosaccharides and Molar Ratios in 100 mL of the Hydrolyzate of the High-Molecular Polysaccharide

|  | Glucose | Fucose | Rhamnose |
|---|---|---|---|
| Contents μg/100 mL | 608.6 | 317.0 | 338.6 |
| Molar ratio | 2 | 1 | 1 |

B. Recovery of polysaccharide constituents with a molecular weight of about $5 \times 10^4$ or less

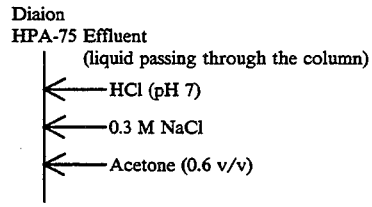

Recovery of low-molecular components
Diaion
HPA-75 Effluent
    (liquid passing through the column)
  ← HCl (pH 7)
  ← 0.3 M NaCl
  ← Acetone (0.6 v/v)

Removal of high molecular component precipitate

Filtration
  ← Acetone (Total 1.5 v/v)

Crystal analysis

Centrifugal precipitation
(5000 r.p.m. × 10 min)

Dissociation

Washing with acetone

Vacuum-drying

TABLE 4

|  | Elemental Analysis | | | |
|---|---|---|---|---|
|  | C | H | N | Moisture |
| Low-molecular polysaccharide | 20.28 | 3.70 | 0.18 | 4.1 |
|  | 23.46 | 4.39 | 0.18 |  |
|  | 20.75 | 3.00 | 0.15 |  |

Figure 12:
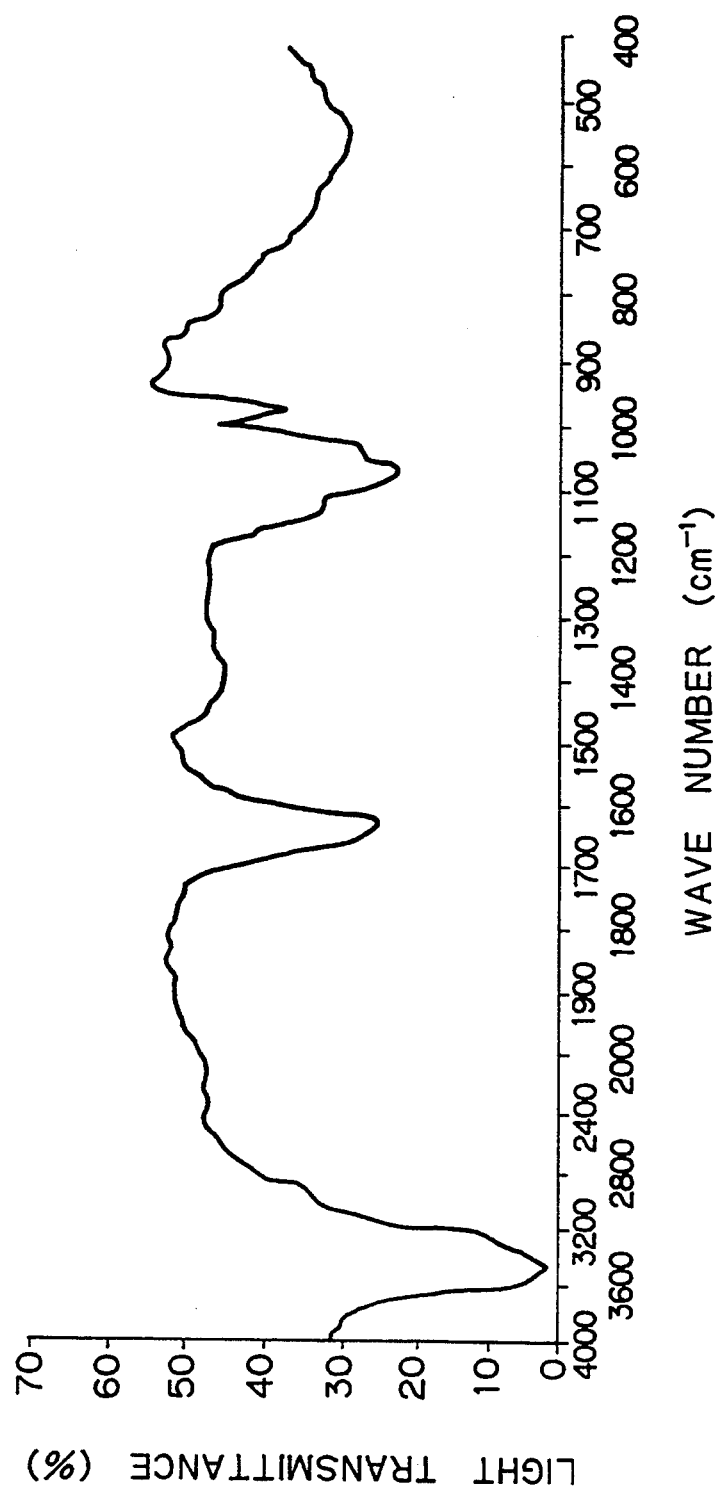
FIG. 12 is an IR absorption spectrum of the polymer of low molecular components obtained in accordance with the present invention.
Figure 13A:
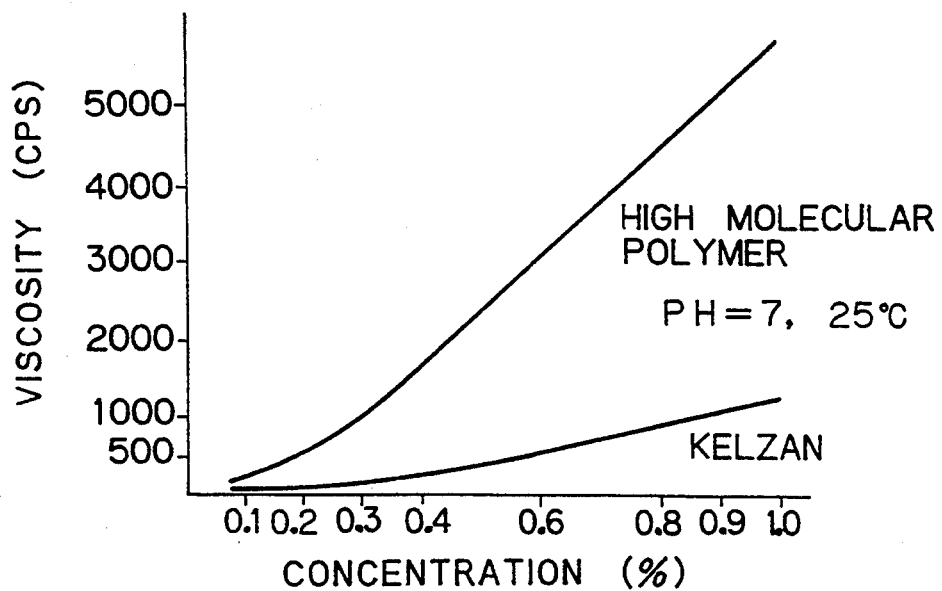
FIG. 13 is a graph showing the relationship between the concentration and the viscosity of the aqueous solution of the material treated with an organic solvent. As controls were used a non-treated high polymer and Kelzan. The vertical axis plots the viscosity (cps) and the horizontal axis plots the polymer concentration (wt/wt%).
Figure 13B:
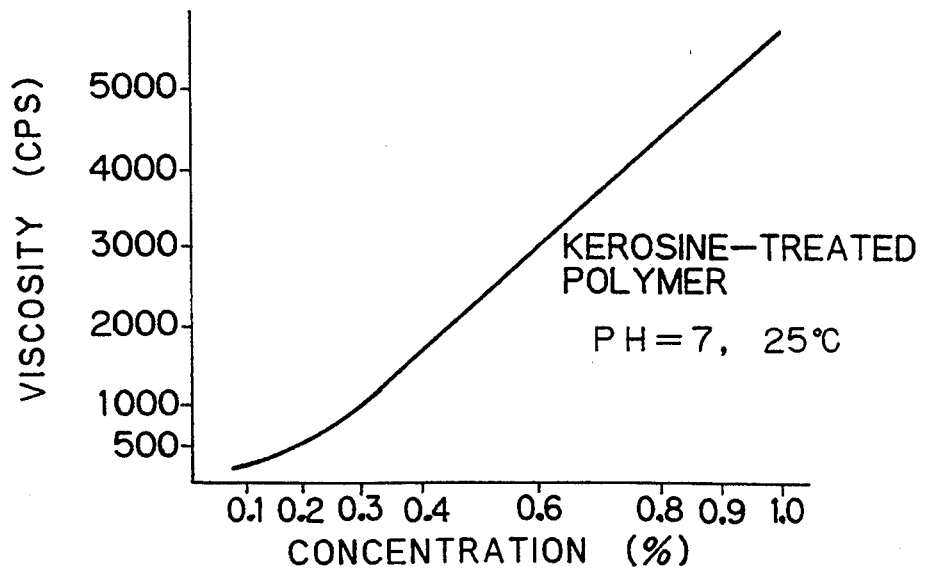
Figure 13C:
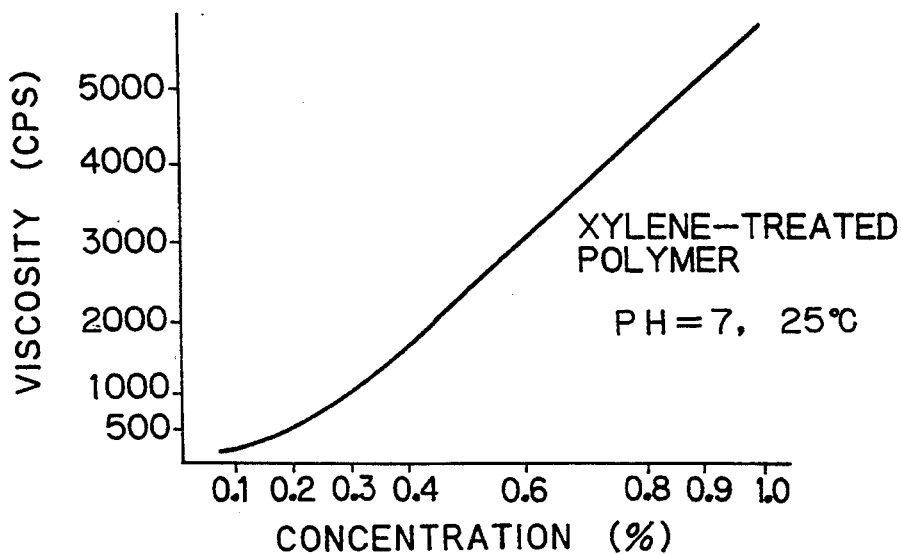
Figure 13D:
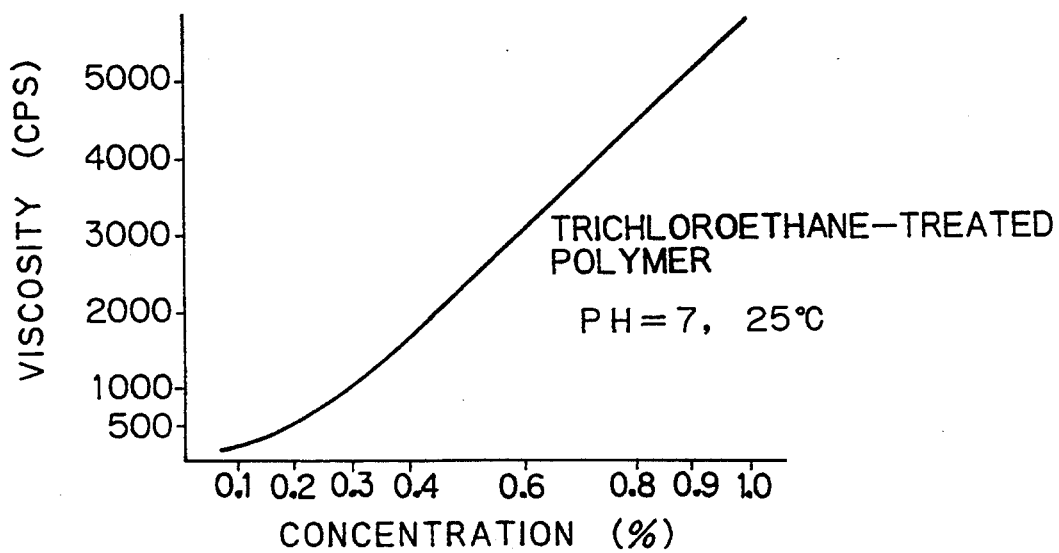
Figure 13E:
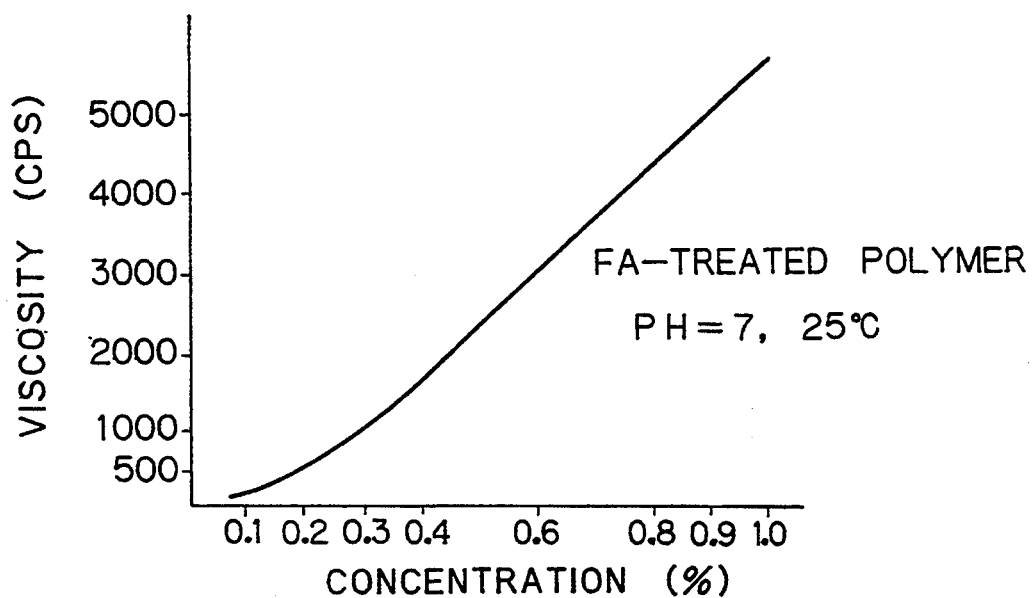
Figure 13F:
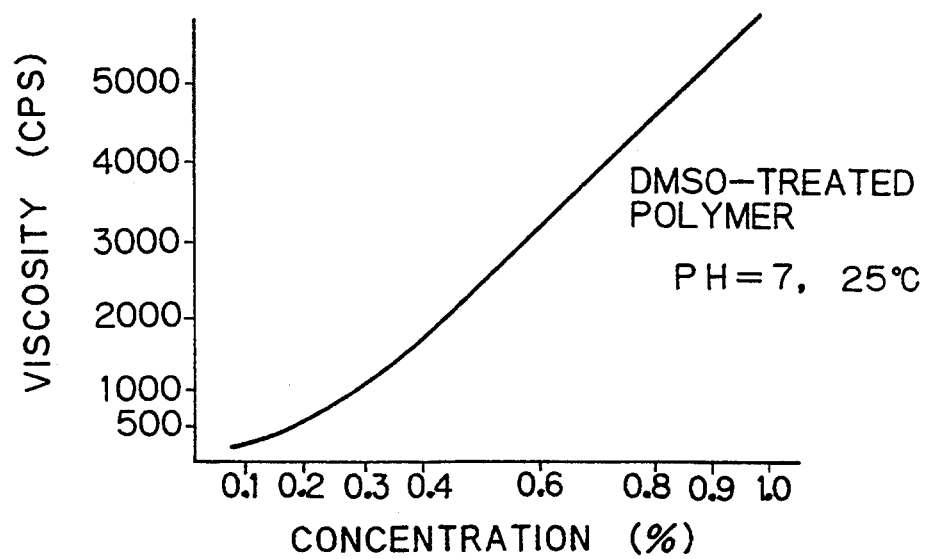

Further, the IR absorption spectrum of the obtained low-molecular polysaccharide is shown in FIG. 12.

Example 2

The high-molecular polymer prepared in Example 1 was made into a powdery, dried material by means of a spray dryer (manufactured by Tokyo Rika, temperature at the inlet: 120°˙C., temperature at the crown: 80° C.). 1 g of the high-molecular polymer powder was put into 1,000 mL of kerosene. It was subjected to an ultrasound homogenizer for 3 minutes so that it should be dispersed well. After it was heated at 70° C. for 2 hours, it was cooled spontaneously. Then, the high-molecular polymer was precipitated to be recovered by means of a centrifuge (20,000G, 20 minutes). The resultant polymer was washed with n-hexane several times and vacuum-dried. This was used as a kerosene-treated sample. 1 g of the high-molecular polymer was put into 1,000 mL of xylene. In the same manner as in kerosene, the high-molecular polymer was dispersed and heated, recovered by means of a centrifuge, washed with acetone and vacuum-dried. This was used as a xylene-treated sample. Subsequently, in the same manner as above, the high-molecular polymer was dispersed into trichloroethane, heated, recovered by means of a centrifuge, washed with chloroform, vacuum-dried and recovered. This was used as a trichloroethane-treated sample. 1 g of the high-molecular polymer was put into 1,000 g of formamide, heated at 70° C. and stirred for 2 hours. The high-molecular polymer dissolved and its viscosity increased. Subsequently, the high-molecular polymer was vacuum-dried at 70° C. to evaporate formamide completely. This was used as a formamide-treated sample.

Next, in the same manner as above, 1 g of the high-molecular polymer was put into 1,000 g of dimethyl sulfoxide, heated at 70° C. and stirred. It dissolved in the same manner is formamide. Then, dimethyl sulfoxide was completely evaporated. The resultant product was used as a dimethyl surfoxide-treated sample.

Regarding the kerosene-treated sample, the trichloroethane-treated sample, the xylene-treated sample, the formamide (FA)-treated sample and the dimethyl surfoxide (DMSO)-treated sample prepared in Example 2, their water absorption properties, moisture retention properties, moisture absorption properties and thickening properties were examined.

Example 3

Water absorption properties were measured.

A method generally referred to as a "tea bag method" was adopted. A container having a capacity of about 20 mL was made from a non-woven fabric ("Kitchen Tauper" of Tokai Pulp Co., Ltd., 100% natural pulp) and charged with a predetermined weight of a sample such as a dried polymer. Then, the container was immersed in pure water for 2 hours, recovered and left to stand for 1 hour to remove the surplus water. The dehydrated sample was put into a constant weight beaker (10 mL) and its weight after water absorption (the weight of water absorbed+sample's weight) was measured exactly. Thereafter, the sample was dried at 105° C. for 15 hours to evaporate water completely. The exact weight of the sample was again measured.

After these measurements, the amount of water absorption (g) per gram of the dried sample was calculated by the following equation. As comparative samples, five samples shown in Table 5 were selected.

$$\begin{aligned} \text{Water absorption} &= [\text{weight after water absorption (g)} - \\ &\quad \text{weight before water absorption (g)}]/ \\ &\quad \text{dried sample weight} \\ (&= \text{weight before water absorption})(g) \end{aligned}$$

According to Table 6, high-molecular polymers treated with an organic solvent showed high water absorption properties equal to those of non-treated ones.

TABLE 5

| Comparative sample | Manufacturer | Remarks |
| --- | --- | --- |
| Silica gel | Kanto Chemicals Co., Ltd. | Reagent |
| Ion-exchange resin | Dow Chemical | |
| High-grade water-absorbing polymer | Sumitomo Chemical | Sumika Gel S-50 |
| PVA | Unitika Kasei | UP-100G, 8–10 cps, partially saponified |
| Anionic polymer | Sumitomo Chemical | Sumifloc FA-70 (acrylamide/acrylic acid copolymer; M-7 × 10$^6$) |

TABLE 6

Water Absorption of Biopolymers

| | Sample | Water absorption (g) per g of a dried sample |
| --- | --- | --- |
| Test group | Organic solvent-treated sample | |
| | Kerosene-treated sample | 1,245 |
| | Xylene sample | 1,183 |
| | Trichloroethane sample | 1,321 |
| | FA sample | 1,284 |
| | DMSO sample | 1,219 |
| | Non-treated polymer | |
| | High-molecular polymer | 1,308 |
| Control group | Silica Gel | 1.4 |
| | Ion-exchange resin | 2.5 |
| | High-grade water-absorbing polymer | 249.4 |
| | PVA | 4.6 |
| | Anionic polymer | 363.6 |

Example 4

Moisture absorbing capability was measured in accordance with the method described in Koshokaishi (J. of Perfume and Cosmetics), Vol. 8, No. 2, p. 131 (1984) as the following. Desiccators respectively containing a saturated solution of potassium nitrate (relative humidity: 91%), a saturated solution of sodium nitrate (relative humidity: 61.8%) and a saturated solution of magnesium chloride (relative humidity: 31.9%) were used as stored in a thermostatic chamber at 37° C. 100 mg of each dry sample were weighed precisely into a plastic cup with an inner diameter of 1.2 cm (manufactured by Sanko Plastics) and left to stand in the desiccator. After 2, 4, 6, 8 and 24 hours, the weights of the samples were measured and the percentages of moisture absorbed by these samples were determined by the following equation.

Percentage or moisture absorption
$(\%) = [(W_t - W_o)/W_o] \times 100$ $W_o$: weight before standing
$W_t$: weight measured at given intervals As shown in Table 7, polymers treated with organic solvents showed high moisture absorption properties equal to those of non-treated ones.

TABLE 7

| Relative humidity | Sample | Moisture absorption at given intervals (hour) | | | | | | |
| --- | --- | --- | --- | --- | --- | --- | --- | --- |
| | | 2 | 4 | 6 | 8 | 10 | 24 | 48 |
| 91% | High-molecular polymer | 42 | 53 | 61 | 65 | 69 | 93 | 105 |
| | Kerosene-treated polymer | 38 | 50 | 58 | 62 | 66 | 87 | 99 |
| | Xylene polymer | 39 | 52 | 62 | 61 | 68 | 91 | 104 |
| | Trichloroethane polymer | 40 | 53 | 60 | 62 | 67 | 89 | 103 |
| 61.8% | FA polymer | 43 | 51 | 59 | 65 | 69 | 87 | 101 |
| | DMSO polymer | 41 | 53 | 60 | 65 | 69 | 92 | 105 |
| | Glycerin | 33 | 49 | 61 | 68 | 76 | 113 | 140 |
| | PEG 200 | 27 | 38 | 45 | 50 | 55 | 78 | 92 |
| | Anionic polymer | 17 | 28 | 35 | 41 | 46 | 64 | 75 |
| | Hyaluronic | | | | | | 35 | |

TABLE 7-continued

| Relative humidity | Sample | Moisture absorption at given intervals (hour) | | | | | | |
|---|---|---|---|---|---|---|---|---|
| | | 2 | 4 | 6 | 8 | 10 | 24 | 48 |
| 61.8% | High-molecular polymer | 31 | 33 | 34 | 33 | 34 | 33 | 35 |
| | Kerosene-treated polymer | 28 | 30 | 31 | 32 | 32 | 31 | 30 |
| | Xylene polymer | 29 | 32 | 32 | 33 | 33 | 34 | 35 |
| | Trichloroethane polymer | 33 | 34 | 35 | 35 | 35 | 35 | 37 |
| | FA polymer | 31 | 32 | 33 | 33 | 34 | 35 | 35 |
| | DMSO polymer | 32 | 34 | 34 | 35 | 35 | 35 | 36 |
| | Glycerin | 23 | 30 | 33 | 35 | 36 | 37 | 38 |
| | PEG 200 | 18 | 20 | 20 | 20 | 20 | 20 | 22 |
| | Anionic polymer | 9 | 13 | 16 | 21 | 21 | 22 | 21 |
| | Hyaluronic acid | | | | | | | 17 |
| 31.9% | High-molecular polymer | 7 | 9 | 6 | 11 | 12 | 12 | 11 |
| | Kerosene-treated polymer | 9 | 10 | 7 | 14 | 14 | 14 | 14 |
| | Xylene polymer | 8 | 9 | 10 | 11 | 12 | 12 | 12 |
| | Trichloroethane polymer | 9 | 10 | 11 | 12 | 13 | 14 | 14 |
| | FA polymer | 8 | 9 | 10 | 13 | 14 | 14 | 13 |
| | DMSO polymer | 7 | 9 | 10 | 13 | 14 | 14 | 14 |
| | Glycerin | 6 | 9 | 11 | 12 | 13 | 12 | 12 |
| | PEG 200 | 3 | 7 | 7 | 7 | 7 | 6 | 7 |
| | Anionic polymer | 1 | 1 | 1 | 2 | 1 | 3 | 4 |

Example 5

The method of measuring moisture retention capability is described in Koshokaishi, ibid. Desiccators respectively containing a saturated solution of sodium nitrate (relative humidity: 64.8%), a saturated solution of magnesium chloride (relative humidity: 33%) and phosphorus pentoxide (relative humidity: 34%) were used as stored in a thermostatic chamber at 20° C.

Additional desiccators respectively containing a saturated solution of sodium sulfate (relative humidity: 64.8%) and silica gel were used as stored in a thermostatic chamber at 20° C. About 100 mg of each dry sample were weighed precisely into a plastic cup and 20 $\mu$L of water was added therein. The resultant mixture was weighed precisely again and left to stand in the desiccator. The weight of each sample after the standing was measured according to the moisture absorption test and moisture retention capability was calculated according to the following equation with the percentage of residual water being used as an index.

Percentage of residual water
$(\%) = [1-(W_o-W_t)/20] \times 100$ $W_o$: weight of the hydrous sample before the standing
$Wt_t$: weight of the hydrous sample measured at given intervals As shown in Table 8. samples treated with organic solvents showed high moisture retention capability.

TABLE 8

| Relative humidity | Sample | Moisture absorption at given intervals (hour) | | | | | | |
|---|---|---|---|---|---|---|---|---|
| | | 2 | 4 | 6 | 8 | 10 | 24 | 48 |
| 64.8% | High-molecular | 155 | 159 | 162 | 163 | 168 | 167 | 162 |
| | Kerosene-treated polymer | 160 | 161 | 164 | 167 | 172 | 171 | 167 |
| | Xylene polymer | 157 | 159 | 162 | 168 | 169 | 168 | 167 |
| | Trichloroethane polymer | 158 | 160 | 164 | 168 | 170 | 170 | 165 |
| | FA polymer | 159 | 161 | 163 | 169 | 171 | 171 | 163 |
| | DMSO polymer | 160 | 161 | 165 | 170 | 170 | 169 | 168 |
| | Glycerin | 156 | 178 | 189 | 195 | 203 | 207 | 200 |
| | PEG 200 | 140 | 141 | 144 | 146 | 150 | 151 | 143 |
| | Anionic polymer | 96 | 99 | 103 | 105 | 111 | 111 | 105 |
| | Hyaluronic acid | | | | | | 105 | |
| | High-molecular polymer | 100 | 99 | 96 | 95 | 97 | 84 | 82 |
| | Kerosene-treated polymer | 97 | 94 | 89 | 88 | 90 | 86 | 84 |
| | Xylene polymer | 98 | 97 | 92 | 91 | 90 | 85 | 83 |
| | Trichloroethane polymer | 99 | 98 | 93 | 92 | 93 | 86 | 82 |
| | FA polymer | 99 | 97 | 94 | 91 | 90 | 84 | 81 |
| | DMSO polymer | 100 | 95 | 92 | 90 | 89 | 82 | 82 |
| | Glycerin | 79 | 76 | 72 | 72 | 74 | 58 | 55 |
| | PEG 200 | 66 | 61 | 57 | 56 | 58 | 46 | 43 |
| | Anionic polymer | 43 | 37 | 36 | 35 | 36 | 33 | 33 |
| 34% measured under $P_2O_5$ | High-molecular polymer | 51 | 32 | 24 | 26 | 24 | 26 | 9 |
| | Kerosene-treated polymer | 56 | 40 | 36 | 34 | 34 | 26 | 17 |
| | Xylene polymer | 52 | 38 | 34 | 29 | 26 | 25 | 11 |

TABLE 8-continued

| Relative humidity | Sample | Moisture absorption at given intervals (hour) | | | | | | |
|---|---|---|---|---|---|---|---|---|
| | | 2 | 4 | 6 | 8 | 10 | 24 | 48 |
| | Trichloroethane polymer | 55 | 32 | 30 | 28 | 24 | 23 | 13 |
| | FA polymer | 53 | 39 | 32 | 28 | 24 | 23 | 14 |
| | DMSO polymer | 54 | 31 | 29 | 26 | 23 | 22 | 14 |
| | Glycerin | 39 | 24 | 20 | 18 | 16 | 4 | −2 |
| | PEG 200 | 23 | 12 | 15 | 19 | 11 | 14 | −31 |
| | Anionic polymer | 30 | 25 | 22 | 21 | 20 | 16 | 10 |

Example 6

The viscosity vs concentration characteristics of the polymers treated with organic solvents prepared in Example 2 were measured. As controls, the polymers containing a high-molecular polysaccharide of Example 1 and Kelzan (general-purpose xanthan gum of Kelco Co.) all particles of which passed a 28-mesh screen were used. Each of the samples and controls was dissolved in pure water at a concentration of 1% (wt/wt) and thereafter diluted with pure water at varying concentration from 0.1 to 1%. The viscosity of he respective dilutions was measured with a Brookfield type viscometer (25° C. and 30 rpm on No. 2 spindle). The results are shown in FIG. 13(A)-(F). The samples treated with an organic solvent showed higher thickening effects than Kelzan as non-treated ones.

Example 7

Solutions containing 2000 ppm of the polymers treated with organic solvents used in Example 2, an aqueous solution containing 200 ppm of the polymer containing a high-molecular polysaccharide of Example 1 and an aqueous solution containing 4000 ppm of Kelzan were prepared. The rotational speed of No. 2 spindle in a Brookfield type viscometer (DH 7.2 and 25° C.) was varied between 6 rpm and 60 rpm and the resulting changes in the viscosity of each solution were measured.

Figure 14A:
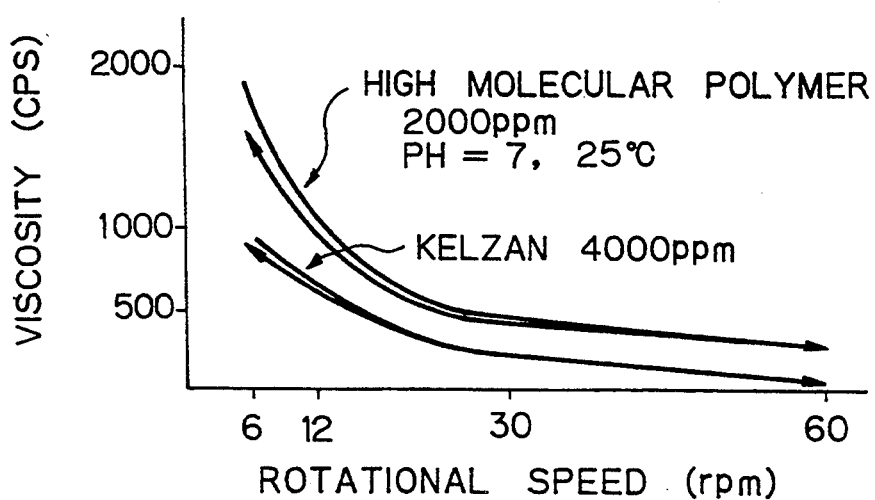
FIG. 14 shows fluidity curves for aqueous solutions of polymers. The vertical axes plot the viscosity (cps) and the horizontal axes plot the rotational speed of spindles.
Figure 14B:
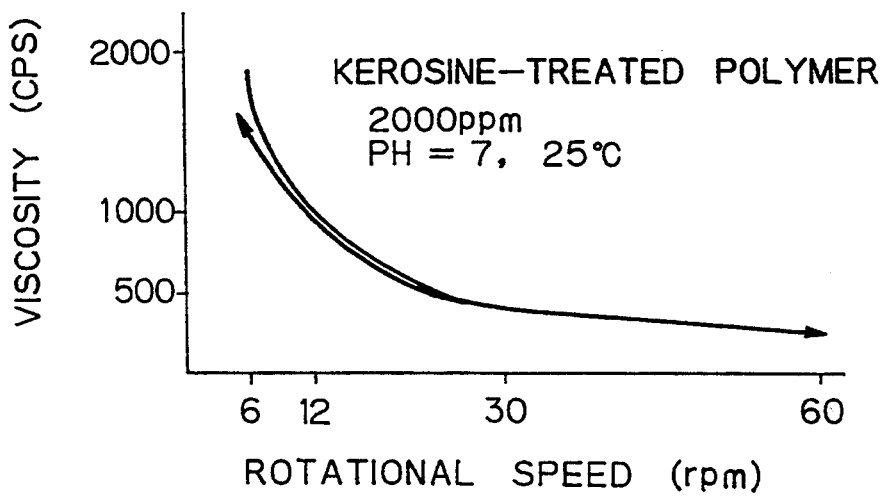
Figure 14C:
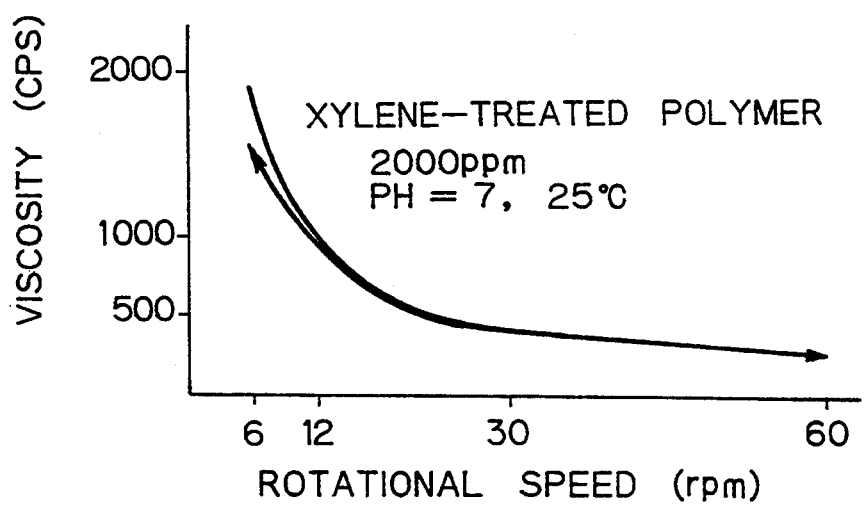
Figure 14D:
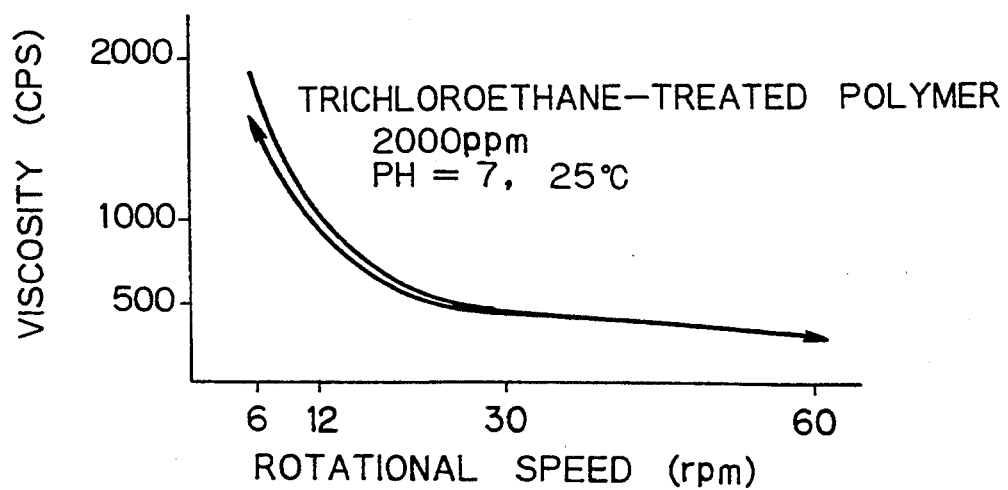
Figure 14E:
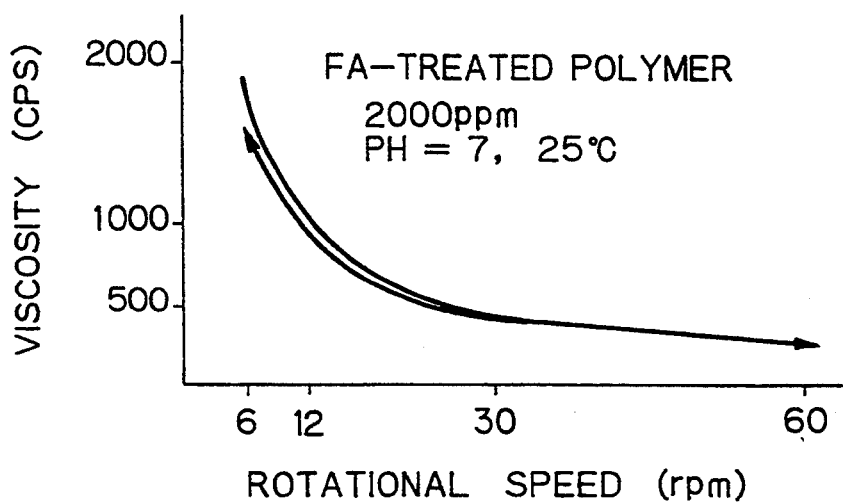
Figure 14F:
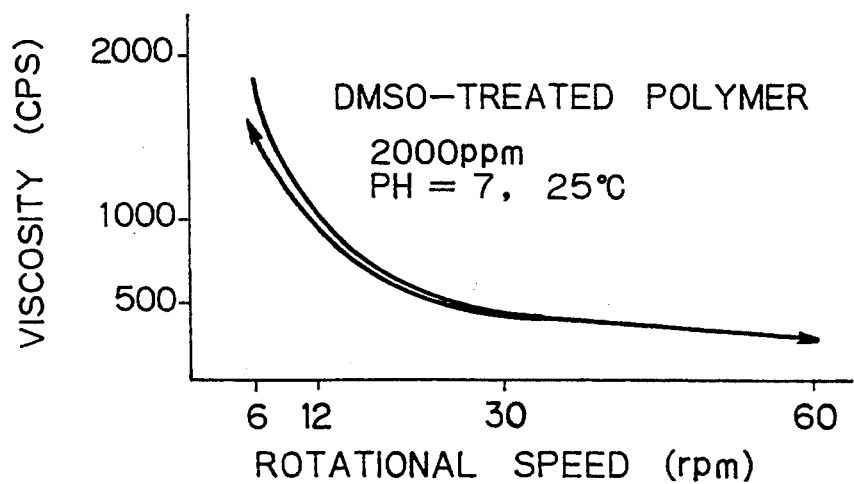

The results for the samples treated with organic solvents are shown in FIG. 14(B)-(F) and those for the non-treated sample and Kelzan are shown in FIG. 14(A), from which one can see that pseudoplastic properties are not lost by being treated with an organic solvent.

Example 8

I loopful of strain B-16 grown on a buillon agar culture medium (meat extract 0.7%, peptone 1%, NaCl 0.3%, agar 2%) was inoculated into a 300-mL conical flask containing 50 mL of the medium I shown in Table 9 and cultured under shaking at 30° C. for 24 hours. 10 mL of the culture broth was inoculated into a II conical flask containing 300 mL of the medium II of the following Table and cultured under shaking at 30° C. for 24 hours. Subsequently, the whole culture broth was inoculated into a 5 L jar containing 2700 ml of the medium II shown in Table 9 (concentration: concentration after the inoculation) and cultured at 500 rpm with an air amount of 3 L/min, at a temperature of 30° C. for 120 hours. After the completion or the culture, said polysaccharide was obtained according to the ethanol precipitation method described in Japanese Patent Public Disclosure No. 291292/1990. The dry weight was measured and 9.0 g/L of the polysaccharide was accumulated.

TABLE 9

| Medium I (g/L) | | Medium II (g/L) | |
|---|---|---|---|
| Glucose | 20 | Glucose | 20 |
| $KH_2PO_4$ | 4.5 | $KH_2PO_4$ | 4.5 |
| $K_2HPO_4$ | 1.5 | $K_2HPO_4$ | 1.5 |
| NaCl | 0.1 | NaCl | 0.1 |
| $MgSO_4.7H_2O$ | 0.2 | $MgSO_4.7H_2O$ | 0.2 |
| Urea | 1 | Urea | 1 |
| Yeast extract | 0.5 | Ile, Met, Pro, | 0.1 |
| pH | 7.2 | Leu, His | (each) |
| | | Tyr | 0.01 |
| | | *Metallic salt mixtures | |
| | | pH | 7.2 |

*Metallic salt mixtures:
$FeSO_4.7H_2O$ 990 μg/L, $ZnSO_4.7H_2O$ 880 μg/L,
$CuSO_4.5H_2O$ 393 μg/L, $MnCl_2.4_2O$ 72 μg/L,
$Na_2B_4O_7.10H_2O$ 88 μg/L, $(NH_4)_6Mo_7O_{24}.4H_2O$ 37 μg/L

Example 9

Strain B-16 grown on a buillon agar culture medium (meat extract 0.7%, peptone 1%, NaCl 0.3%, agar 2%) was inoculated into a 300-mL conical flask containing 100 mL of a modified culture medium of the medium II shown in Example 8 (instead of Ile, Met, Pro, Leu and His, amino acids of Ala, Set, Gly, Val, Lys, Arg, Ile, Met, Pro, Leu, His, Glu, Thr, Asp, Cys, Phe and Trp were added at a concentration of 0.1 g/L, and the concentration of glucose was changed to 10 g/L) and cultured at a temperature of 30° C. for 10 days. After the completion of the culture, said polysaccharide was obtained according to the ethanol precipitation method described in Japanese Patent Public Disclosure No. 291292/1990. The dry weight was measured and 2.5 g/L of the polysaccharide were accumulated.

Example 10

Strain B-16 grown on a buillon agar culture medium (meat extract 0.7%, peptone 1%, NaCl 0.3%, agar 2%) was inoculated into a 300 mL conical flask containing 100 mL of a modified culture medium of the medium II shown in Example 8 (instead of Ile, Met, Pro, Leu, His and Tyr was added Gly at a concentration of 0.1 g/L, the concentration of glucose was changed to 10 g/L and 10 mg/L of $CaCl_2$ were added) and cultured at a temperature of 30° C. for 10 days. After the completion of the culture, said polysaccharide was obtained according to the ethanol precipitation method described in Japanese Patent Public Disclosure No. 291292/1990. The dry weight was measured and 2.3 g/L of the polysaccharide were accumulated.

As a control, culture was conducted on the culture medium except metallic salt mixtures and $CaCl_2$. Only 0.5 g/L of the polysaccharide was accumulated.

Example 11

Using a medium modifying the composition of the medium II of Example 8 (instead of metallic salt mixtures was added FeSO$_4$.7H$_2$O at a concentration of 10 mg/L), the same test as in Example 8 was carried out. As a result, 8.9 g/L of the polysaccharide were accumulated.

Example 12

Using a medium modifying the composition of the medium II of Example 8 (instead of Ile, Met, Pro, Leu, His and Tyr, amino acids of Gly, Cit, Arg, Met, Glu, and Ile were added at a concentration of 0.1 g/L, and instead of metallic salt mixtures was added FeSO$_4$.7H$_2$O at a concentration of 10 mg/L), the same test as in Example 8 was carried out. As a result, 7.9 g/L of the polysaccharide were accumulated.

Example 13

Using a medium modifying the composition of the medium II of Example 8 (instead of Ile, Met, Pro, Leu, His and Tyr was added Gly at a concentration of 0.6 g/L), the same test as in Example 8 was carried out. As a result, 7.7 g/L of the polysaccharide were accumulated.

Example 14

Using a medium modifying the composition of the medium II of Example 8 (instead of Ile, Met, Pro, Leu, His and Tyr was added Gly at a concentration of 0.6 g/L and instead of metallic salt mixtures was added FeSO$_4$.7H$_2$O at a concentration of 10 mg/L), the same test as in Example 8 was carried out. As a result, 8.9 g/L of the polysaccharide were accumulated.

As a control, culture was conducted on the culture medium except FeSO$_4$.7H$_2$O. Only 1.1 g/L of the polysaccharide were accumulated.

Example 15

Culture was carried out using the same procedure as in Example 9 except that fructose, sucrose or maltose was used instead of glucose in a modified culture medium of the medium II in Example 9. In the culture broths was accumulated the polysaccharide in an amount of 2.3 g/L, 2.1 K/L and 2.2 g/L, respectively.

Example 16

Culture was carried out using the same procedure as in Example 9 except that the modified culture medium of the medium II of Example 9 was replaced with a modified culture medium of the medium I of Table 9 in which yeast extract was changed to polypeptone or CSL. In the culture broths was accumulated the polysaccharide in an amount of 2.1 K/L and 2.0 g/L respectively.

Example 17

Culture was carried out using the same procedure as in Example 9 except that the modified culture medium of the medium II of Example 9 was replaced with a modified culture medium of the medium I of Table 9 in which glucose was changed to fructose, sucrose or maltose. In the culture broths was accumulated the polysaccharide in an amount of 1.9 K/L, 2.0 g/L and 2.1 g/L, respectively.

Referential Example

According to the medium I (natural medium) and the medium II (synthetic medium) of Example 8, the properties of the culture products described in Example 8 are as follows:

| Elemental analysis | Natural medium | Synthetic medium |
| --- | --- | --- |
| C | 36.48 | 35.74 |
| H | 6.68 | 6.29 |
| N | 0.05 | 0.03 |
| Protein (Lowry method) | 0.7% | 0.4% |
| Nucleic acid | 0.2% | 0.0% |

| Constituent sugar ratio | Natural medium | Synthetic medium |
| --- | --- | --- |
| Fucose | 1 | 1 |
| Rhamnose | 1.8 | 1.7 |
| Glucose | 2.2 | 2.9 |
| Glucuronic acid | 1 | 1 |
| Mannose | 0.2 | 0.1 |

Glucornic acid is according to a sulfate carbazole method and others according to gas chromotography.

| Water absorption properties | Natural medium | Synthetic medium |
| --- | --- | --- |
| Water | 1.245 g | 1.124 g |
| Saline solution (0.9 wt %) | 345 g | 320 g |

Water absorbing capability

A method generally referred to as a "tea bag method" was adopted. A container having a capacity of about 20 mL was made from a non-woven fabric ("Kitchen Tauper" of Tokai Pulp Co., Ltd.; 100% natural pulp) and charged with a predetermined weight of a sample such as a dried polymer. Then, the container was immersed in pure water for 2 hours, recovered and left to stand for 1 hour to remove the surplus water. The dehydrated sample was put into a constant weight beaker (10 mL) and its weight after water absorption (the weight of water absorbed+sample's weight) was measured exactly. Thereafter, the sample was dried at 105° C. for 2 hours to completely evaporate the water. The exact weight of the sample was again measured.

After these measurements, the amount of water absorption (g) per gram of the dried sample was calculated by the following equation:

$$\text{Water absorption} = \frac{\text{sample weight after absorption (g)} - \text{sample weight before absorption (g)}}{\text{dried sample's weight}}$$

(= sample weight before absorption) (g)

Figure 15A:
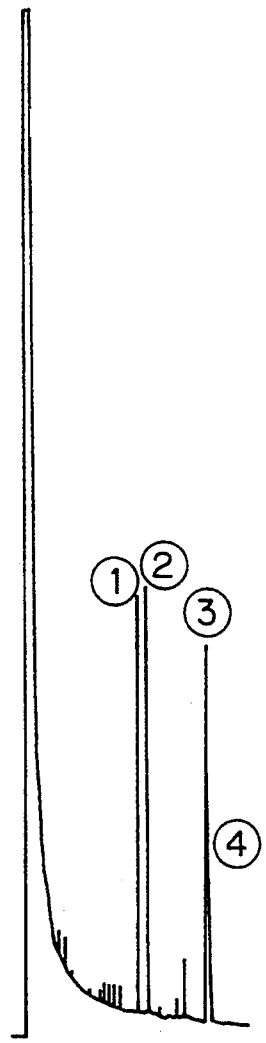
FIG. 15(A) and (B) show gas chromatography charts for the constituent monosaccharides of the culture products according to a natural medium and a synthetic medium, respectively.
Figure 15B:
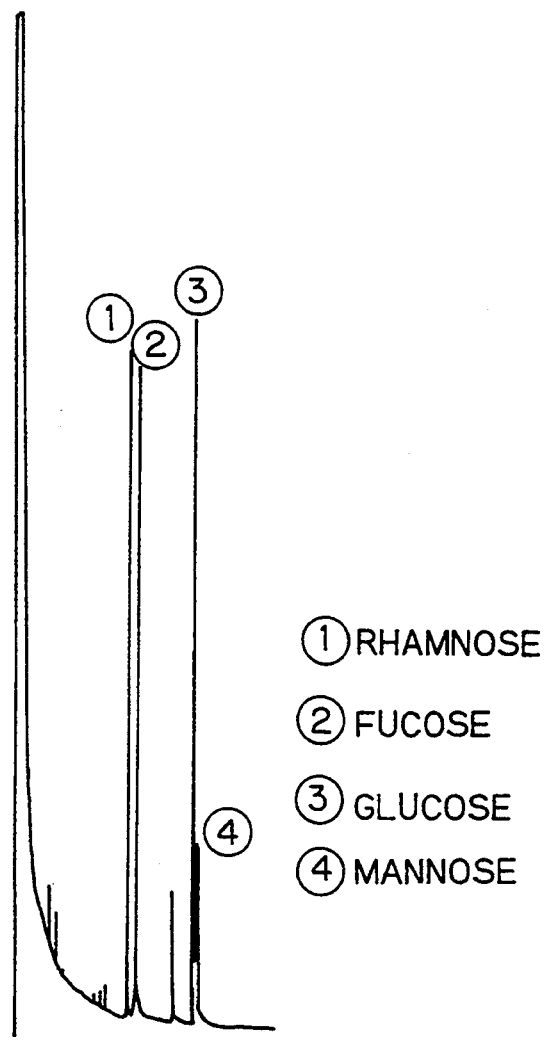

The gas chromatographic charts of the constituent monosaccharide of the culture products according to the above natural medium and synthetic medium are shown in FIG. 15(A) and (B) respectively.

Figure 16A:
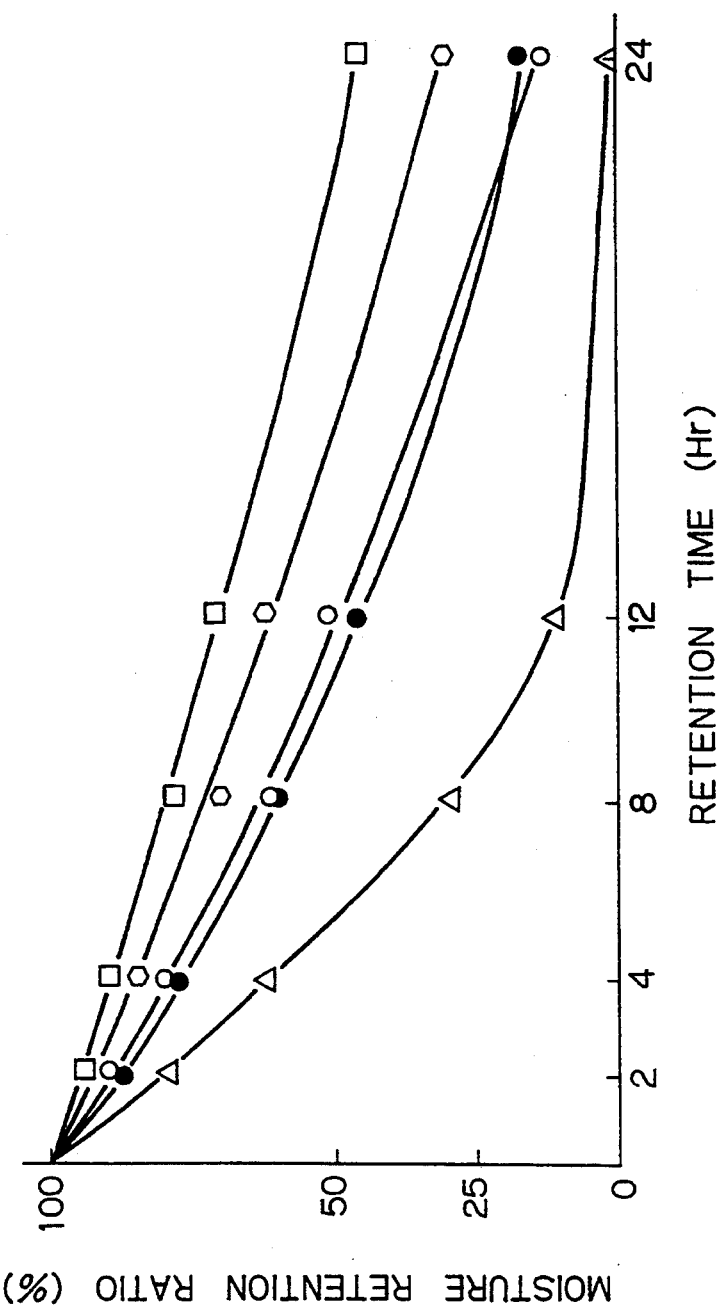
FIG. 16(A) and (B) show the relationship between the retention time and the moisture retention ratio at the relative humidity of 64.8% and 33%, respectively.
Figure 17:
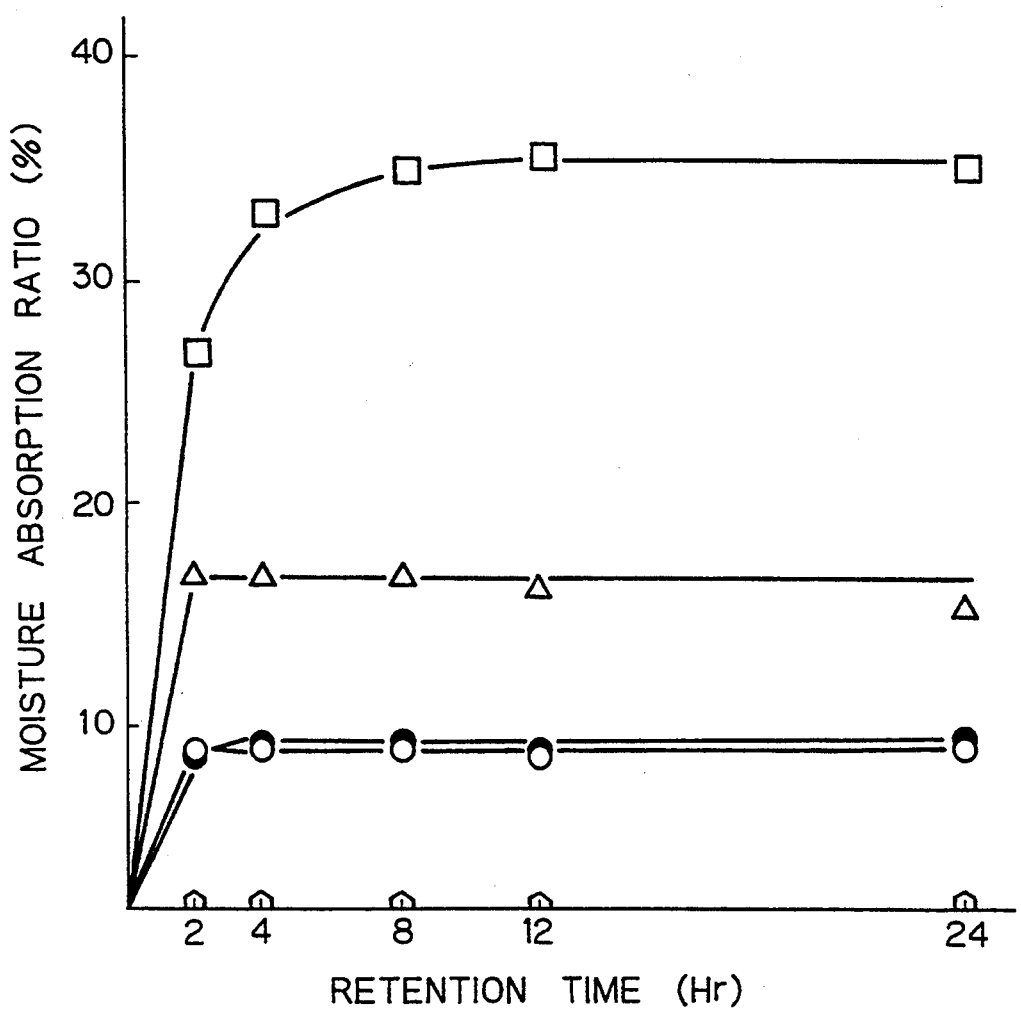
FIG. 17 shows the relationship between the retention time and the moisture absorption ratio.
Figure 18:
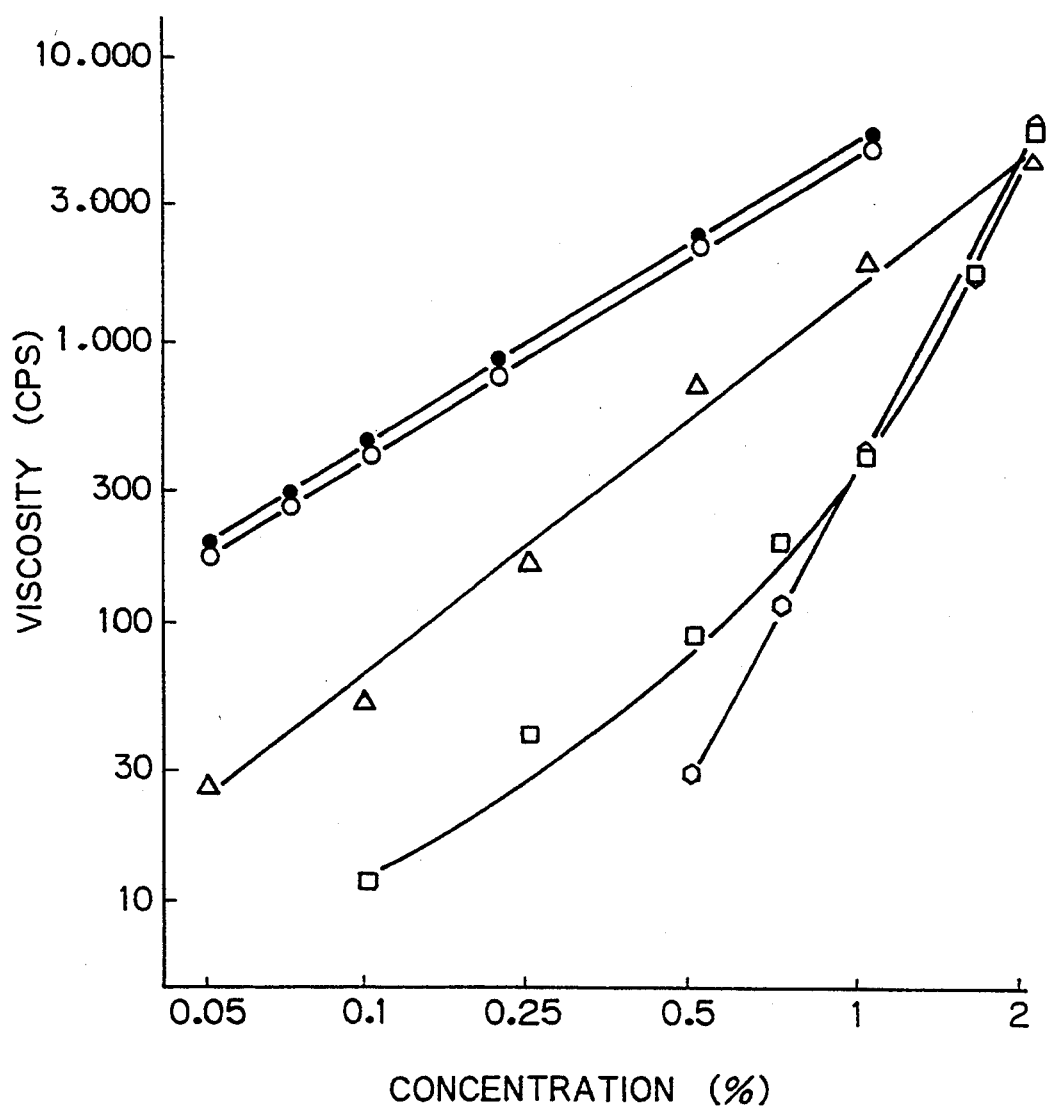
FIG. 18 shows the relationship between the concentration and the viscosity of each thickening agent solution.
Figure 19:
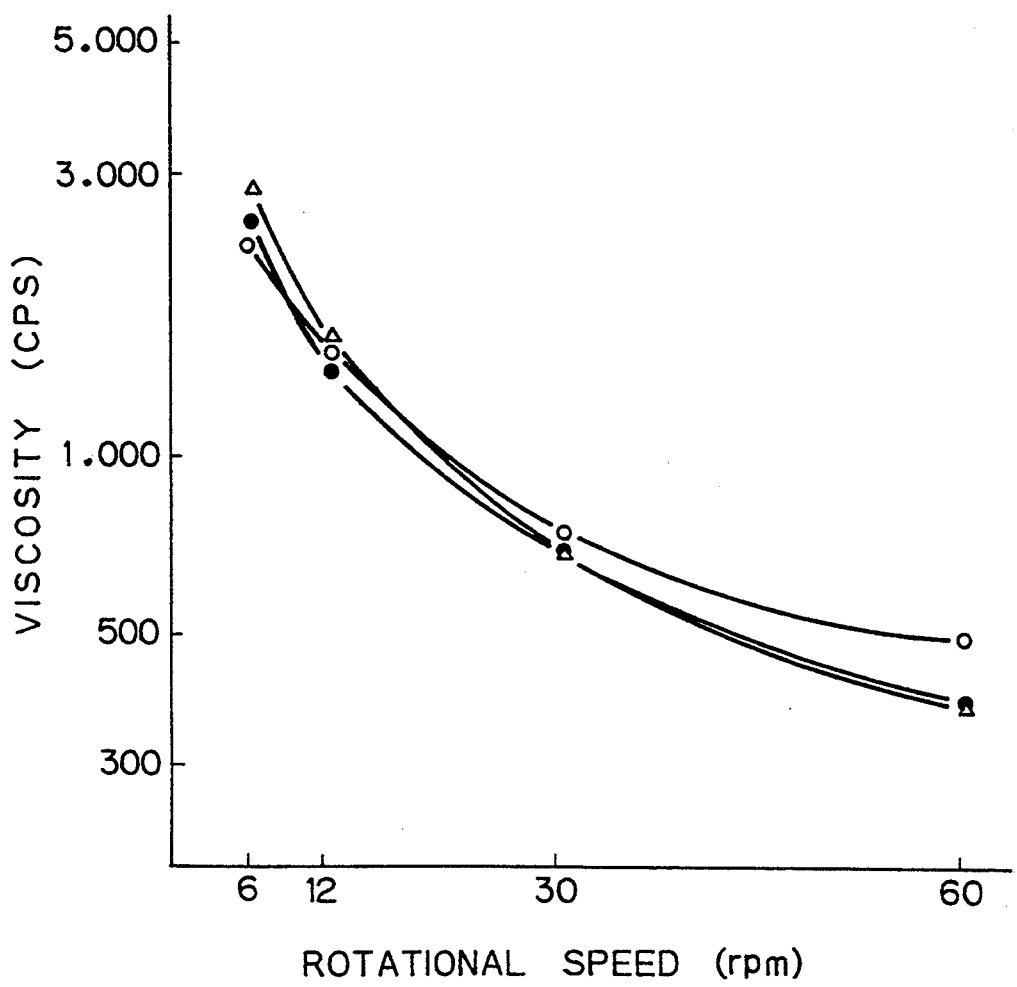
FIG. 19 shows the non-Newtontian viscosity according to the relationship between the rotational speed and the apparent viscosity.

With respect to moisture retention properties, the relationship between the retention time (hour) and the retention percentage (%) is shown by the contrast between FIG. 16(A) (relative humidity: 64.8%-NANO$_3$ saturated solution) and FIG. 16(B) (relative humidity: 33%-MgCl$_2$ saturated solution) at 20° C., sample:-water=1:10 (initial setting), known substance, wherein
○: B-16 natural
△: PVP,
●: B-16 synthetic
□: Glycerin,
◯: Urea, With respect to moisture absorption properties, the relationship between the retention time (hour) and the moisture absorption percentage (%) is shown in FIG. 17, wherein
Relative humidity: 61.8% (NaNO$_3$ saturated solution) 37° C.
○: B-16 natural,
△: PVP,
●: B-16 synthetic,
□: Glycerin,
◯: Urea With respect to viscosity, the relationship between the concentration (%) and the viscosity (CPS) of each thickening agent solution is shown in FIG. 18, wherein
Measurement of viscosity: Brookfield type viscometer, 30 rpm, 30° C.
○: B-16 natural,
●: B-16 synthetic,
◯: MC,
△: xanthan gum,
□: sodium alginate According to the measurement of the relationship between the rotational speed (rpm) and the apparent viscosity (CPS), the non-Newtonian viscosity is shown as FIG. 19, wherein
Measurement of viscosity: Brookfield type viscometer, 30° C.
○: B-16 I 0.2% natural
●: B-16 A 0.2% synthetic,
△: xanthan gum 0.5%

Following are examples of the applications to which the material of the present invention may be put.

Food applications:
Thickeners, fillers, water retainers, texture improving agents, dietary foods;

Feedstuff applications:
Thickeners, fillers, water retainers, carrier entrapping;

Medical applications:
immunoactivators, drug entrapping (e.g., capsules and tablets);

Biotechnological applications:
Immobilizers for use in bioreactors, etc., culture bases for microorganisms, plants and animal cells, supports (gels) for separation and purification;

Agricultural applications:
Capsules of slow release agents (e.g., agrichemicals), suspension stabilizers, emulsion stabilizers, improving adhesion, improving dust-ability, controlling the shape of liquid droplets;

Civil engineering:
Soil improving agents, soil water retainers, mud stabilizers, soil stabilizers;

Distribution:
Drip absorbents for use in foods such as fish and meat;

Paper coating:
Improving the performance of coatings, preventing migration, preventing streaks, preventing pigment sedimentation, improving water retention;

Textile dyeing:
Preventing pigment sedimentation, preventing migration, improving dye fluidity of space dyeing;

Latices:
Emulsion stabilizers;

Cleaners:
Emulsion stabilizers, suspension stabilizers, antisagging agents, improving sprayability;

Suspension stabilizers:
Stabilizing TiO$_2$ suspensions, stabilizing the suspensions of starch slurry;

Foam stabilizers:
Foamed cement;

Improvement of polishing agents:
Buffing agents;

Paint improving agents:
Improving theological properties.

Industrial Applicability

As is apparent from the above, the polymer of the present invention shows an excellent water absorbing capability, moisture absorbing capability, moisture retaining capability and thickening capability even after it is dispersed or dissolved and heated in various organic solvents. Thus, since the polymer of the present invention has excellent microorganism-derived biodegradability and shows resistance to organic solvents, it is a material which has a wide range of applications in the form of synthetic high molecules and can be formed into a safe product free from secondary pollution and which has water absorption properties, water retention properties and moisture retention properties of its original properties.

In addition, in the fermentation and production of polysaccharides, they can be produced by using a natural medium or a synthetic medium comprising a saccharide, an inorganic salt, an amino acid mixed solution and a trace metal salt mixed solution as medium components.

We claim:

1. A polysaccharide having the following properties:
   (A) sugar composition as determined by thin-layer chromatography, liquid chromatography and gas chromatography:
   the principal constituents are rhamnose, fucose, glucose and glucuronic acid which are present in a molar ratio of (1–4):2:(1–8):(1–4);
   (B) elemental analysis (wt %):
   (said polysaccharide containing 9–13% of crystalline water)
   C: 36±3
   H: 7±1
   O: 56±4;
   (C) solubility:
   slightly soluble in water (neutral); soluble in alkalies; insoluble in methanol, ethanol and acetone;
   (D) UV absorption spectrum:
   no absorption detected at 280 nm characteristic of proteins (peptides) or at 260 nm characteristic of nucleic acids; and
   (E) IR absorption spectrum:
   an absorption pattern characteristic of polysaccharides is observed near 800–1200 cm$^{-1}$; CH and CH$^2$ absorption patterns due to carbohydrates are observed near 2950 cm$^{-1}$; and an OH absorption pattern due to carbohydrates is observed near 3400±20 cm$^{-1}$.

2. A polysaccharide according to claim 1 wherein a molecular weight of the polysaccharide according to liquid chromatography is $1 \times 10^6$ or more.

3. A polysaccharide composition which comprises (1) a culture of an *Alcaligenes* microorganism or a product obtained by treating said culture with an organic solvent, and (2) a polysaccharide according to claim 1 or claim 2.

4. A composition according to claim 3 wherein said Alcaligenes microorganism is *Alcaligenes latus* strain B-16 (FERM BP-2015).

* * * * *

UNITED STATES PATENT AND TRADEMARK OFFICE
CERTIFICATE OF CORRECTION

PATENT NO. : 5,378,832
DATED : January 3, 1995
INVENTOR(S) : Ryuichiro Kurane et al It is certified that error appears in the above-indentified patent and that said Letters Patent is hereby corrected as shown below:

On the title page, item:

[73] Assignees: Japan as represented by Director General of Agency of Industrial Science and Technology; Hakuto Co., Ltd.; Kyowa Hokkoh Kogyo Co., Ltd., all of Tokyo, Japan Signed and Sealed this Fourteenth Day of November, 1995

*Attest:*

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,378,832
DATED : January 3, 1995
INVENTOR(S) : RYUICHIRO KURANE ET AL It is certified that error appears in the above-indentified patent and that said Letters Patent is hereby corrected as shown below:

On the title page, item [73] should read as follows:

[73] Assignees: Japan as represented by Director General of Agency of Industrial Science and Technology; Hakuto Co., Ltd.; Kyowa Hakkoh Kogyo Co., Ltd., all of Tokyo, Japan This certificate supersedes Certificate of Correction issued November 14, 1995.

Signed and Sealed this

Seventeenth Day of June, 1997

Attest:

BRUCE LEHMAN

Attesting Officer

Commissioner of Patents and Trademarks